(12) United States Patent
Biesinger et al.

(10) Patent No.: US 12,396,664 B1
(45) Date of Patent: Aug. 26, 2025

(54) INVESTIGATION OF GLYCEMIC EVENTS IN BLOOD GLUCOSE DATA

(71) Applicant: Verily Life Sciences LLC, Mountain View, CA (US)

(72) Inventors: William Jacob Benhardt Biesinger, Fremont, CA (US); Joshua Burkart, Boston, MA (US); Nathan Dickerson Beach, Somerville, MA (US); Shih-Yo Cheng, Milpitas, CA (US)

(73) Assignee: Verily Life Sciences LLC, Dallas, TX (US)

( * ) Notice: Subject to any disclaimer, the term of this patent is extended or adjusted under 35 U.S.C. 154(b) by 11 days.

(21) Appl. No.: 18/402,670

(22) Filed: Jan. 2, 2024

Related U.S. Application Data

(63) Continuation of application No. 17/402,290, filed on Aug. 13, 2021, now Pat. No. 11,883,163, which is a
(Continued)

(51) Int. Cl.
*G16H 40/40* (2018.01)
*A61B 5/00* (2006.01)
(Continued)

(52) U.S. Cl.
CPC ........ *A61B 5/14532* (2013.01); *A61B 5/7282* (2013.01); *G16H 15/00* (2018.01); *G16H 40/40* (2018.01); *G16H 40/63* (2018.01)

(58) Field of Classification Search
CPC .. A61B 5/14537; A61B 5/7282; G16H 15/00; G16H 40/40; G16H 40/63
(Continued)

(56) References Cited

U.S. PATENT DOCUMENTS

| | | | | |
|---|---|---|---|---|
| 5,695,949 | A | * | 12/1997 | Galen ...................... C12Q 1/34 435/14 |
| 6,553,386 | B1 | * | 4/2003 | Alabaster ............... G16H 10/20 434/137 |

(Continued)

OTHER PUBLICATIONS

Albers, David J., et al., "Personalized glucose forecasting for type 2 diabetes using data assimilation", "Personalized glucose forecasting for type 2 diabetes using data assimilation;" PLoS Comput Biol 13(4): e1005232. https://doi.org/10.1371/journal.pcbi.1005232; Apr. 27, 2017;, Apr. 27, 2017, 1-38.
(Continued)

*Primary Examiner* — Michael Tomaszewski
(74) *Attorney, Agent, or Firm* — Perkins Coie LLP

(57) ABSTRACT

To better understand the impact of glycemic events, some entities have begun examining the relationship between the blood glucose level and another physiological parameter. However, this relationship can be difficult to understand. Introduced here are computer programs and associated computer-implemented techniques for discovering glycemic events in a series of data values representative of blood glucose measurements and then altering the measurement schedule of a sensor capable of generating measurements in a dimension other than blood glucose based on the glycemic events. By altering the measurement schedule of the sensor, a diabetes management platform can better understand how, if at all, dimensions other than blood glucose are related to the glycemic health state of a subject whose blood glucose level is being monitored.

20 Claims, 17 Drawing Sheets

Related U.S. Application Data continuation of application No. 16/380,959, filed on Apr. 10, 2019, now Pat. No. 11,089,980, which is a continuation-in-part of application No. 16/249,633, filed on Jan. 16, 2019, now Pat. No. 11,475,988, and a continuation-in-part of application No. 15/891,291, filed on Feb. 7, 2018, now Pat. No. 10,624,591.

(60) Provisional application No. 62/618,474, filed on Jan. 17, 2018.

(51) Int. Cl.
    *A61B 5/145*     (2006.01)
    *G16H 15/00*     (2018.01)
    *G16H 40/63*     (2018.01)

(58) Field of Classification Search
    USPC .......................................................... 705/2–3
    See application file for complete search history.

(56) References Cited

U.S. PATENT DOCUMENTS

| | | | |
|---|---|---|---|
| 7,727,147 B1* | 6/2010 | Osorio | A61M 5/14244 600/347 |
| 8,249,946 B2* | 8/2012 | Froseth | G06Q 10/101 426/103 |
| 8,597,570 B2* | 12/2013 | Terashima | A61B 5/4866 600/347 |
| 10,624,591 B1 | 4/2020 | Biesinger et al. | |
| 11,089,980 B1* | 8/2021 | Biesinger | G16H 40/60 |
| 11,166,670 B1* | 11/2021 | Bikhchandani | A61B 5/7267 |
| 11,278,668 B2* | 3/2022 | Gupta | A61M 5/1723 |
| 11,883,163 B1* | 1/2024 | Biesinger | A61B 5/7282 |
| 12,171,547 B2 | 12/2024 | Constantin et al. | |
| 2002/0032583 A1* | 3/2002 | Joao | G16H 15/00 705/2 |
| 2002/0158775 A1* | 10/2002 | Wallace | H04B 3/54 340/870.07 |
| 2003/0208113 A1 | 11/2003 | Mault et al. | |
| 2003/0235817 A1 | 12/2003 | Bartkowiak et al. | |
| 2005/0027182 A1* | 2/2005 | Siddiqui | G16H 15/00 128/903 |
| 2005/0038332 A1* | 2/2005 | Saidara | G16H 40/67 128/920 |
| 2005/0143635 A1* | 6/2005 | Kamath | A61B 5/14532 600/347 |
| 2006/0258929 A1* | 11/2006 | Goode | A61B 5/14865 600/365 |
| 2007/0167853 A1* | 7/2007 | Melker | A61B 5/411 600/529 |
| 2007/0276209 A1 | 11/2007 | Emoto et al. | |
| 2008/0045819 A1 | 2/2008 | Emoto et al. | |
| 2008/0056946 A1* | 3/2008 | Ahmad | C12Q 1/26 422/68.1 |
| 2008/0154513 A1* | 6/2008 | Kovatchev | G16H 15/00 702/19 |
| 2008/0201169 A1* | 8/2008 | Galasso | G16H 40/63 705/2 |
| 2008/0208027 A1* | 8/2008 | Heaton | G16H 40/63 600/365 |
| 2008/0255438 A1* | 10/2008 | Saidara | A61B 5/14532 600/365 |
| 2009/0105568 A1* | 4/2009 | Bugler | A61B 5/14865 600/347 |
| 2009/0105572 A1 | 4/2009 | Malecha | |
| 2009/0105573 A1 | 4/2009 | Malecha | |
| 2009/0177068 A1 | 7/2009 | Stivoric et al. | |
| 2009/0177147 A1 | 7/2009 | Blomquist et al. | |
| 2010/0286607 A1* | 11/2010 | Saltzstein | A61B 5/02455 604/93.01 |
| 2011/0004085 A1* | 1/2011 | Mensinger | A61B 5/7275 600/365 |
| 2011/0225112 A1 | 9/2011 | Cameron et al. | |
| 2013/0035871 A1 | 2/2013 | Mayou et al. | |
| 2013/0282396 A1 | 10/2013 | Lagor | |
| 2013/0325504 A1* | 12/2013 | Greene | G06T 11/206 705/3 |
| 2014/0068487 A1 | 3/2014 | Steiger et al. | |
| 2014/0128705 A1 | 5/2014 | Mazlish | |
| 2014/0188398 A1 | 7/2014 | Cohen et al. | |
| 2014/0253323 A1* | 9/2014 | Berven | G08B 21/02 340/539.12 |
| 2015/0045641 A1* | 2/2015 | Rule | A61B 5/150229 600/347 |
| 2015/0141770 A1* | 5/2015 | Rastogi | A61B 5/1459 600/595 |
| 2015/0289823 A1* | 10/2015 | Rack-Gomer | A61B 5/6898 600/365 |
| 2016/0378937 A1* | 12/2016 | Soni | G06F 18/23 705/3 |
| 2017/0053101 A1 | 2/2017 | Booth et al. | |
| 2017/0071513 A1 | 3/2017 | Hoss et al. | |
| 2017/0128007 A1* | 5/2017 | Hayter | G09B 5/02 |
| 2017/0185748 A1 | 6/2017 | Budiman et al. | |
| 2017/0220751 A1 | 8/2017 | Davis et al. | |
| 2017/0308981 A1 | 10/2017 | Razavian et al. | |
| 2017/0329917 A1 | 11/2017 | Mcraith et al. | |
| 2018/0150757 A1 | 5/2018 | Aggarwal et al. | |
| 2018/0197628 A1* | 7/2018 | Wei | G16H 20/60 |
| 2019/0008461 A1* | 1/2019 | Gupta | G06N 5/01 |
| 2019/0175079 A1 | 6/2019 | Nishida et al. | |
| 2019/0175080 A1 | 6/2019 | Varsavsky et al. | |
| 2019/0290172 A1 | 9/2019 | Hadad et al. | |

OTHER PUBLICATIONS

Lim, Teck-Onn , et al., "Bimodality in Blood Glucose Distribution", "Bimodality in Blood Glucose Distribution; Is it universal?"; Clinical Research Centre, the Department of Nephrology, and the Public Health Institute, Kuala Lumpur, Malaysia; Apr. 10, 2002; pp. 2212-2217;, 2212-2217.

Mttinghoff, Eric , et al., "Regression Methods in Biostatistics", Regression Methods in Biostatistics: Linear, Logistic, Survival, and Repeated Measures Models; ISBN 0-387-20275-7; San Francisco, CA; Oct. 2004;, 346 pages.

* cited by examiner

1100

1101
Acquire physiological data generated by a glucose monitoring device

1102
Post a visualization of the physiological data as a glucose trace over time to an interface for review by an individual 1103
Examine the physiological data to detect an excursion in the blood glucose level 1104
Classify the excursion as being indicative of a glycemic event 1105
Identify an annotation corresponding to the glycemic event 1106
Cause display of the annotation on the interface accessible to the individual 1107
Store an indication of the annotation in a database to create a historical record of annotations associated with a subject

FIGURE 11

INVESTIGATION OF GLYCEMIC EVENTS IN BLOOD GLUCOSE DATA

CROSS-REFERENCE TO RELATED APPLICATIONS

This application is a continuation of U.S. application Ser. No. 17/402,290, titled "Investigation of Glycemic Events in Blood Glucose Data" and filed Aug. 13, 2021, which is a continuation of U.S. application Ser. No. 16/380,959, titled "Investigation of Glycemic Events in Blood Glucose Data" and filed on Apr. 10, 2019, now U.S. Pat. No. 11,089,980, that issued Aug. 17, 2021, which is a continuation-in-part of U.S. application Ser. No. 15/891,291, titled "Annotations of Continuous Glucose Monitoring Data" and filed on Feb. 7, 2018, now U.S. Pat. No. 10,624,591 that issued Apr. 21, 2020, each of which is incorporated herein by reference in its entirety.

U.S. application Ser. No. 16/380,959 is also a continuation-in-part of U.S. application Ser. No. 16/249,633, titled "Imputation of Blood Glucose Monitoring Data" and filed on Jan. 16, 2019, now U.S. Pat. No. 11,475,988 that issued Oct. 18, 2022, which claims priority to U.S. Provisional Application No. 62/618,474, titled "Imputation of Blood Glucose Monitoring Data" and filed on Jan. 17, 2018, each of which is incorporated herein by reference in its entirety.

TECHNICAL FIELD

Various embodiments concern computer programs and associated computer-implemented techniques for altering the measurement schedule of a sensor based on the glycemic event(s) discovered in a series of blood glucose values.

BACKGROUND

After ingestion of a foodstuff that contains carbohydrates, the human body breaks down the carbohydrates into glucose, which serves as a source of energy for the cells of the human body. Glucose is transported via circulation within the blood stream. Therefore, ingestion of foodstuffs will influence the concentration of glucose within the blood stream (also referred to as the "blood glucose level" or "glucose level").

According to the American Diabetes Association (ADA), a normal blood glucose level for people without diabetes is below 6.9 mmol/L (125 mg/dL). Meanwhile, the target blood glucose range for people with diabetes is 5.0-7.2 mmol/L (90-130 mg/dL) before meals and less than 10 mmol/L (180 mg/dL) after meals. However, some people with diabetes struggle to consistently stay within the recommended range.

BRIEF DESCRIPTION OF THE DRAWINGS

Various features of the technology will become more apparent to those skilled in the art from a study of the Detailed Description in conjunction with the drawings. Embodiments of the technology are illustrated by way of example and not limitation in the drawings, in which like references may indicate similar elements.

FIG. 11 depicts a flow diagram of a process for discovering signal features in physiological data specifying the blood glucose level of a subject whose glycemic health state is being monitored.

Figure 1:
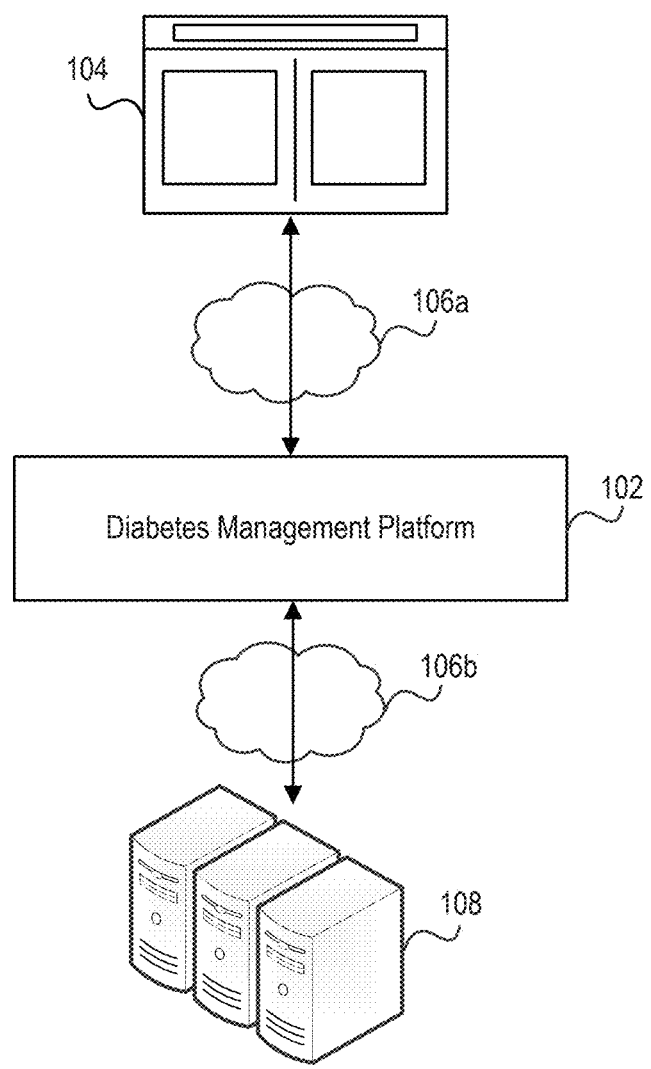
FIG. 1 illustrates a network environment that includes a diabetes management platform.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Diabetes mellitus (commonly referred to as "diabetes") is a group of metabolic disorders in which the affected individuals experience high blood glucose levels over a prolonged period. If left untreated, diabetes can cause many complications. For example, long-term complications can include cardiovascular disease, stroke, chronic kidney disease, foot ulcers, and eye damage.

Blood glucose monitoring is the process through which the concentration of glucose within the blood stream (also referred to as the "blood glucose level" or "glucose level") is tested. A test is typically performed by piercing the skin to draw blood, and then applying the blood to a disposable, chemically-active test strip. Historically, an individual with diabetes would take several measurements throughout the day in an ad hoc manner using a blood glucose meter. Because blood glucose meters require that individuals manually perform each test, measurements are often generated sporadically. However, it can be difficult to establish the blood glucose level between these discrete measurements.

Continuous glucose monitoring represents a promising new way for individuals to gain insights into the diabetes disease state. In contrast to a blood glucose meter, a continuous glucose monitor can continually monitor the blood glucose level throughout the day. For example, a continuous glucose monitor may automatically take blood glucose measurements every five minutes, ten minutes, etc. Thus, an individual may be able to observe how consumption of a certain foodstuff or performance of a certain activity affects blood glucose level.

Individuals with diabetes can benefit from gaining a better understanding of how their blood glucose level fluctuates throughout the day. However, it can be difficult to understand blood glucose level measurements, which represent a technical signal indicative of the diabetes disease state. To better understand the impact of glycemic events, some entities have begun examining the relationship between the blood glucose level and another physiological parameter, such as heart rate or blood pressure. However, this relationship can be difficult to understand, especially for physiological parameters that appear to be unrelated.

Introduced here, therefore, are computer programs and associated computer-implemented techniques for discovering glycemic events in a series of data values representative of blood glucose measurements and then altering the measurement schedule of a sensor capable of generating measurements in a dimension other than blood glucose based on the glycemic events. The sensor could be configured to monitor, for example, temperature, humidity, light, movement (e.g., acceleration), position (e.g., elevation or tilt), heart rate, blood pressure, etc. Thus, the sensor may be able to detect, explicitly or implicitly, instances of activity (e.g., walking or running), sleep, etc. For example, instances of sleep may be determined based on movement data generated by an accelerometer (in which case the absence of movement may be indicative of sleep) or physiological data generated by a heart rate sensor (in which case the lowering of the heart rate may be indicative of sleep). Each glycemic event corresponds to a signal feature defined by one or more data values. For example, each glycemic event may correspond to an excursion defined by a pair of semi-global minima and a peak value.

A diabetes management platform can alter the measurement schedule of a sensor in several different scenarios. First, the diabetes management platform may configure the measurement schedule as part of a real-time investigation process. In such embodiments, the diabetes management platform may receive a stream of blood glucose values in real time, identify a glycemic event by examining the blood glucose values, and then configure the measurement schedule based on the glycemic event. Second, the diabetes management platform may configure the measurement schedule as part of a predictive investigation process. In such embodiments, the diabetes management platform may acquire historical blood glucose values, impute blood glucose values for a future time interval based on the historical blood glucose values, identify a potential onset of a glycemic event by examining the imputed blood glucose values, and then configure the measurement schedule based on the imputed blood glucose value(s) supporting the potential onset.

By altering the measurement schedule of the sensor, the diabetes management platform can better understand how, if at all, dimensions other than blood glucose are related to the glycemic health state of a subject whose blood glucose level is being monitored. For example, the diabetes management platform may cause the resolution and/or polling frequency of the sensor to be highest within a predetermined interval of time expected to include a glycemic event. Such action enables the diabetes management platform to gain a better understanding of dimension(s) other than blood glucose level during intervals of time that are relevant to the glycemic health state, as well as conserve power by limiting measurements during intervals of time that are not relevant (or less relevant) to the glycemic health state.

As further described below, the data values that are examined by the diabetes management platform can include explicit data values (also referred to as "explicit measurements"), implicit data values (also referred to as "implicit measurements"), or any combination thereof. For example, a series of data values could include implicit data values interspersed between explicit data values generated by a blood glucose meter. As another example, a series of data values could include explicit data values generated by a continuous glucose monitor followed by implicit data values representative of estimated blood glucose measurements during a future time interval.

Embodiments may be described with reference to particular computer programs, system configurations, networks, etc. However, those skilled in the art will recognize that these features are equally applicable to other computer program types, system configurations, network types, etc. Moreover, the technology can be embodied using special-purpose hardware (e.g., circuitry), programmable circuitry appropriately programmed with software and/or firmware, or a combination of special-purpose hardware and programmable circuitry. Accordingly, embodiments may include a machine-readable medium having instructions that may be used to program a computing device to perform a process for examining physiological data comprising explicit data values and/or implicit data values, discovering excursions in the physiological data, identifying real-world events and/or circumstances corresponding to the excursions, altering a measurement parameter of a sensor based on the excursions, etc.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, devices may be electrically or communicatively coupled to one another despite not sharing a physical connection.

The term "based on" is also to be construed in an inclusive sense rather than an exclusive or exhaustive sense. Thus, unless otherwise noted, the term "based on" is intended to mean "based at least in part on."

The term "module" refers broadly to software components, hardware components, and/or firmware components. Modules are typically functional components that can generate useful data or other output(s) based on specified input(s). A module may be self-contained. A computer program may include one or more modules. Thus, a computer program may include multiple modules responsible for completing different tasks or a single module responsible for completing all tasks.

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Technology Overview

FIG. 1 illustrates a network environment 100 that includes a diabetes management platform 102. Individuals can interface with the diabetes management platform 102 via an interface 104. The diabetes management platform 102 may be responsible for parsing physiological data pertaining to an individual to discover excursions in the blood glucose level, classifying the excursions as glycemic events, configuring the measurement schedule of a sensor capable of generating measurements in a dimension other than blood glucose based on the glycemic events, etc. The diabetes management platform 102 may also be responsible for creating interfaces through which the individual can view physiological data, manage preferences, etc.

Physiological data could specify the blood glucose level of the individual accessing the interface 104 or some other person. For example, in some embodiments the interface 104 enables a person with diabetes (also referred to as a "subject" or a "patient") to view their own physiological data, while in other embodiments the interface 104 enables an individual to view physiological data associated with some other person. The individual may be a health coach responsible for monitoring the glycemic health of the other person. Examples of health coaches include medical professionals (e.g., a physician or nurse), diabetic health counselors, family members of the other person, etc. As further described below, the physiological data may include explicit data values (e.g., those generated by a glucose monitoring device, such as a blood glucose meter or a continuous glucose monitor) and/or imputed data values (e.g., those generated by the diabetes management platform 102 based on past explicit data values). Some interfaces are configured to facilitate interactions between subjects and health coaches, while other interfaces are configured to serve as informative dashboards for subjects.

As noted above, the diabetes management platform 102 may reside in a network environment 100. Thus, the diabetes management platform 102 may be connected to one or more networks 106a-b. The network(s) 106a-b can include personal area networks (PANs), local area networks (LANs), wide area networks (WANs), metropolitan area networks (MANs), cellular networks, the Internet, etc. Additionally or alternatively, the diabetes management platform 102 can be communicatively coupled with computing device(s) over a short-range communication protocol, such as Bluetooth® or Near Field Communication (NFC).

The interface 104 is preferably accessible via some combination of a web browser, desktop application, mobile application, or over-the-top (OTT) application. Accordingly, the interface 104 may be viewed on a personal computer, tablet computer, personal digital assistant (PDA), mobile phone, game console, music player, wearable electronic device (e.g., a watch or fitness accessory), network-connected ("smart") electronic device, (e.g., a television or home assistant device), virtual/augmented reality system (e.g., a head-mounted display), or some other electronic device.

Some embodiments of the diabetes management platform 102 are hosted locally. That is, the diabetes management platform 102 may reside on the computing device used to access the interface 104. For example, the diabetes management platform 102 may be embodied as a mobile application executing on a mobile phone. Other embodiments of the diabetes management platform 102 are executed by a cloud computing service operated by Amazon Web Services® (AWS), Google Cloud Platform™, Microsoft Azure®, or a similar technology. In such embodiments, the diabetes management platform 102 may reside on a host computer server that is communicatively coupled to one or more content computer servers 108. The content computer server(s) 108 can include different types of data, user information (e.g., profiles, credentials, and health-related information such as age, diabetes classification, etc.), and other assets. Such information could also be stored on the host computer server.

Certain embodiments are described in the context of network-accessible interfaces. However, those skilled in the art will recognize that the interfaces need not necessarily be accessible via a network. For example, a computing device may be configured to execute a self-contained computer program that does not require network access. Instead, the self-contained computer program may cause necessary assets (e.g., physiological data, healthcare regimen data, and processing operations) to be downloaded at a single point in time or on a periodic basis (e.g., weekly, daily, or hourly).

Figure 2:
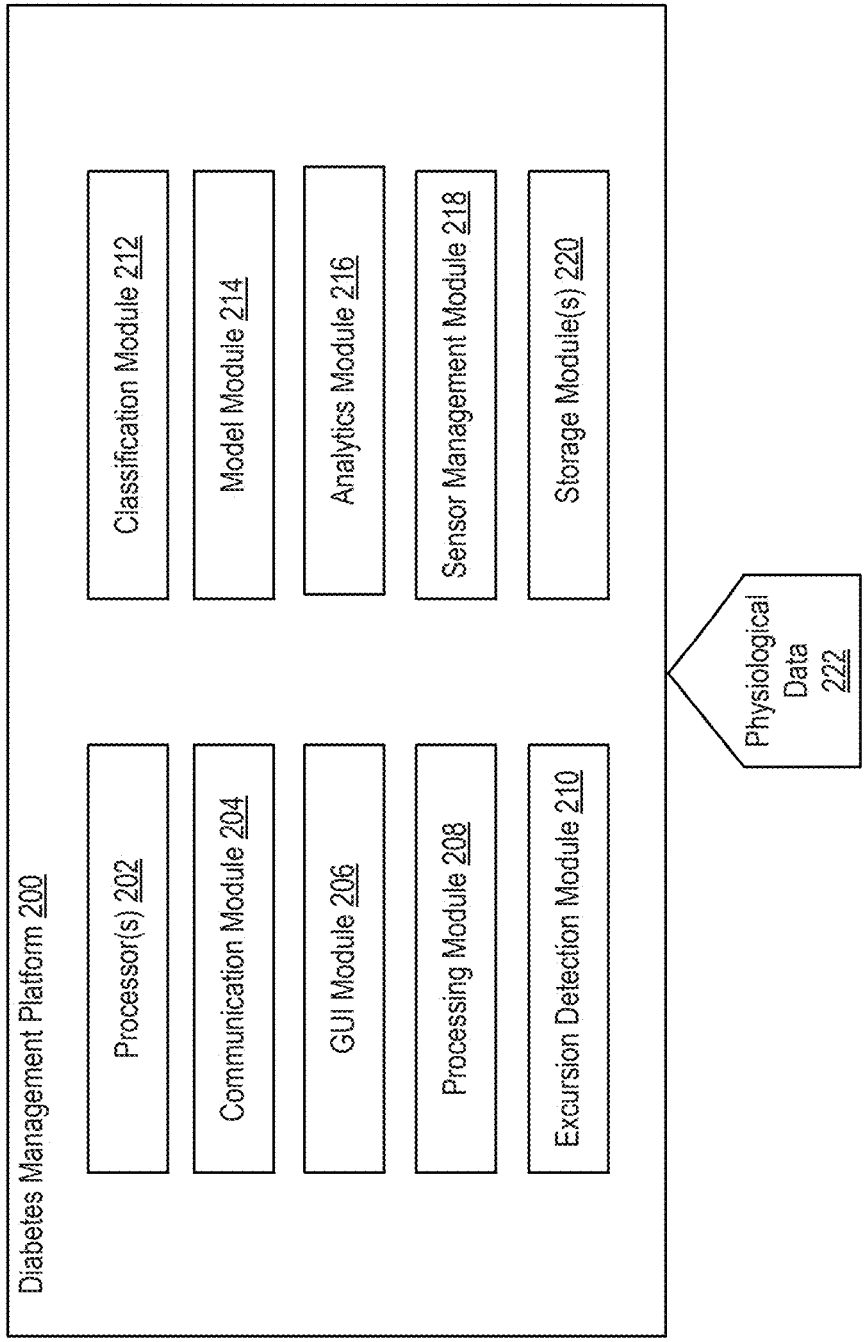
FIG. 2 depicts the high-level architecture of a diabetes management platform able to analyze physiological data to detect excursions in the blood glucose level of a subject that are representative of glycemic events.

FIG. 2 depicts the high-level architecture of a diabetes management platform 200 able to analyze physiological data 222 to detect excursions in the blood glucose level of a subject that are representative of glycemic events. The diabetes management platform 200 may alter the measurement schedule of a sensor based on these excursions. For example, the diabetes management platform 200 may alter the resolution and/or the polling frequency of a sensor configured to monitor, for example, temperature, humidity, light, movement (e.g., acceleration), position (e.g., elevation or tilt), heart rate, blood pressure, etc.

As further described below, the physiological data 222 can include explicit data values and/or imputed data values. Accordingly, the excursions detected by the diabetes management platform 200 may be actual excursions (e.g., as discovered in a real-time stream of explicit data values) or predicted excursions (e.g., as discovered in a real-time stream of imputed data values). In some embodiments the imputed data values reside between explicit data values (e.g., if a subject sporadically measures the blood glucose level using a blood glucose meter), while in other embodiments the imputed data values reside in a future time interval for which there are no explicit data values. Thus, imputed data values can be applied to a personalized statistical model to generate additional data points in between explicit data values. In such embodiments, the personalized statistical model can be trained on historical explicit data values (e.g., measurements generated by a blood glucose meter or a continuous glucose monitor).

As shown in FIG. 1, an individual can interface with the diabetes management platform 200 via an interface. The individual may be a person with diabetes or another person with an interest in the blood glucose level of the person with diabetes.

The diabetes management platform 200 can include one or more processors 202, a communication module 204, a graphical user interface (GUI) module 206, a processing module 208, an excursion detection module 210, a classification module 212, a model module 214, an analytics module 216, a sensor management module 218, and one or more storage modules 220. In some embodiments a single storage module includes multiple computer programs for performing different operations (e.g., format conversion and statistical analysis), while in other embodiments each computer program is hosted within a separate storage module. Embodiments of the diabetes management platform 200 may include some or all of these components, as well as other components not shown here.

The processor(s) 202 can execute modules from instructions stored in the storage module(s) 220, which can be any device or mechanism capable of storing information. For example, the processor(s) 202 may execute the GUI module 206, processing module 208, excursion detection module 210, classification module 212, model module 214, analytics module 216, and sensor management module 218.

The communication module 204 can manage communications between various components of the diabetes management platform 200. The communication module 204 can also manage communications between the computing device on which the diabetes management platform 200 resides and another computing device, sensor, etc.

For example, the diabetes management platform 200 may reside on a mobile phone in the form of a mobile application. In such embodiments, the communication module 204 can facilitate communication with a network-accessible computer server responsible for supporting the mobile application and/or a sensor capable of generating measurements in a dimension other than blood glucose. The communication module 204 may facilitate communication with various data sources through the use of application programming interfaces (APIs), bulk data interfaces, etc.

As another example, the diabetes management platform 200 may reside on a server system that includes one or more network-accessible computer servers. In such embodiments, the communication module 204 can separately communicate with a computer program executing on the computing device associated with the individual and/or the sensor capable of generating measurements in a dimension other than blood glucose. Those skilled in the art will recognize that the components of the diabetes management platform 200 can be distributed between the server system and the computing device associated with the individual in various manners. For example, some data (e.g., physiological data and measurement schedules for the sensor) may reside on the computing device of the individual, while other data (e.g., processing operations for detecting excursions in the physiological data 222 and rule sets for identifying glycemic events, recommendations, etc.) may reside on the server system.

The GUI module 206 can generate the interface(s) through which an individual can interact with the diabetes management platform 200. For example, an interface may include a graphical representation of the blood glucose level over time. The graphical representation may be based on explicit data values, imputed data values, or any combination thereof. As another example, an interface may specify a characteristic of the explicit data values and/or the imputed data values. These interfaces may also present feedback/suggestions for improving the glycemic health state (e.g., by performing certain activities, refraining from consuming certain foodstuffs, etc.).

The processing module 208 can apply one or more operations to the physiological data 222 acquired/generated by the diabetes management platform 200. Physiological data 222 specifying the blood glucose level of an individual could be generated by a glucose monitoring device. Examples of glucose monitoring devices include continuous glucose monitors and blood glucose meters.

A glucose monitoring device may be configured to continuously or periodically transmit physiological data 222 to the diabetes management platform 200. In some embodiments, the glucose monitoring device continually uploads physiological data 222 to the diabetes management platform 200 so long as the glucose monitoring device remains communicatively coupled to the computing device on which the diabetes management platform 200 resides (e.g., via a Bluetooth® communication channel). In other embodiments, the glucose monitoring device uploads physiological data 222 to the diabetes management platform 200 on a periodic basis (e.g., hourly, daily, or weekly). In such embodiments, the physiological data 222 may include multiple data sets (e.g., a first data set for a first time interval, a second data set for a second time interval, etc.). Each time interval could be associated with, and correspond to, a natural rhythm or cycle. Examples of natural rhythms/cycles include a circadian cycle, a menstrual cycle, a feeding cycle, an elimination cycle, etc.

The processing module 208 can process the physiological data 222 into a format suitable for the other modules (e.g., the excursion detection module 210, classification module 212, model module 214, analytics module 216, sensor management module 218, or storage module(s) 220). The processing module 208 can also parse the physiological data 222 to identify certain characteristic(s) of the blood glucose level. For example, the processing module 208 may calculate metrics that are critical in guiding diabetes treatment in a personalized manner. These metrics can include time-in-range, glycemic variability, glycemic exposure, hypoglycemia range, hyperglycemia range, etc.

The excursion detection module 210 can examine the physiological data 222 to detect excursions in the blood glucose level. Each excursion is defined by one or more data values specifying the blood glucose level at corresponding time(s). The excursion detection model 210 can parse the physiological data 222 to detect a signal feature that should be flagged for further analysis. Examples of signal features include:

a minimum blood glucose value;
a maximum blood glucose value (also referred to as a "peak blood glucose value");
a total area beneath the peak blood glucose value (i.e., an integral of a glucose trace over the duration of the peak blood glucose value);
an area beneath the glucose trace during the duration that is outside the glycemic range recommended by the American Diabetes Association (ADA);
a recovery rate following the peak blood glucose value;
a recovery rate following the minimum blood glucose value (e.g., due to consumption of a foodstuff); and a time characteristic of the peak blood glucose value or the minimum blood glucose value.

The recovery rates may be used to determine how symmetric the minimum or peak blood glucose values are. The time characteristic, meanwhile, could be the actual time (e.g., 8:00 AM, 10:30 AM, etc.), the day of the week, or an indication of the time interval. For example, the excursion detection model 210 may simply specify whether a glycemic event occurred during the morning interval, afternoon interval, evening interval, or night interval.

Thus, while some excursions may be defined by blood glucose level variations exceeding a specified amount, other excursions may be based on the magnitude of a single data value (e.g., in the case of the minimum and peak blood glucose values). Similarly, the excursion detection module 210 may identify excursions by applying processing algorithm(s) to identify data value(s) that match a pattern in accordance with a pattern-defining parameter. Additionally or alternatively, the excursion detection module 210 could train a classification model to identify the data value(s) responsive to a determination that a matching window of physiological data corresponds to a foodstuff consumption event (also referred to as a "meal"). A "matching window" is a segment of physiological data 222 that temporally matches the glycemic event. The classification model can be trained using a supervised machine learning algorithm.

The classification module 212 can classify each excursion as being indicative of a glycemic event. For example, the classification module 212 may discover, based on the arrangement of data value(s), that a given excursion is indicative of foodstuff consumption, poor recovery, etc. Because each glycemic event is digitally represented by the data value(s) defining the excursion, a glycemic event can be thought of as a logical categorization of the signal feature and/or the data value(s).

The model module 214 can design a personalized statistical model based on the explicit data values included in the physiological data 222. Using the statistical model, the model module 214 can impute data values representative of estimated blood glucose measurements. The model module 214 can examine explicit data values to identify a feature indicative of a glycemic characteristic of the subject, and then design the statistical model based on the explicit data values, the feature, the glycemic characteristic, or any combination thereof. In some embodiments, each explicit data value corresponds to a time at which the explicit data value was generated. In such embodiments, the model module 214 may also consider the times (also referred to as "time points") when designing the statistical model. Several different models can be designed by the model module 214.

For example, the model module 214 may be configured to construct a Gaussian process model. In such embodiments, the model module 214 can use a radial basis function kernel designed to capture a correlation timescale and a periodic kernel designed to capture typical periodic patterns (e.g., daily, weekly, or monthly patterns). The radial basis function kernel is typically designed to indicate that the blood glucose level is less likely to change over short time intervals (e.g., several seconds) than long time intervals (e.g., several hours). The periodic kernel, meanwhile, can be designed to ensure that imputed data values conform with a periodic pattern of past explicit data values associated with the subject.

As another example, the model module 214 may be configured to construct a Kalman filtering model (also referred to as "linear quadratic estimation model"). In such embodiments, the model module 214 can track variance values indicative of the uncertainty of the imputed data values. By estimating a joint probability distribution over the imputed data values, the model module 214 can increase imputation accuracy over other techniques that are based on a single measurement. The model module 214 can also update the imputed data values and/or the variance values using a state transition model. The state transition model can be based on ordinary differential equation(s) representing the relevant biological responses. In some embodiments the ordinary differential equation(s) are adaptively personalized based on characteristic(s) of the subject, while in other embodiments the ordinary differential equation(s) are statically programmed based on biological literature.

An example of a potential form for an ordinary differential equation is provided by Makroglou et al. in "Mathematical models and software tools for the glucose-insulin regulatory system and diabetes: an overview," *Applied Numerical Mathematics*, 56(3-4):559-573, 2006; Chervoneva et al. in "Estimation of nonlinear differential equation model for glucose-insulin dynamics in type 1 diabetic patients using generalized smoothing," *The Annals of Applied Statistics*, 8(2):886-904, 2014; and De Gaetano et al. in "Mathematical modeling of the intravenous glucose tolerance test," *Journal of Mathematical Biology*, 40(2):136-168, 2000.

$$\frac{dG}{dt} = -b_1 G - b_4 IG + b_7 + S_G(t) \tag{Eq. 1}$$

$$\frac{dI}{dt} = -b_2 I + \frac{b_6}{b_5} \int_{-\infty}^{t} G(s) e^{\frac{s-t}{b_5}} ds + S_I(t) \tag{Eq. 2}$$

where
G Blood glucose level;
I Blood insulin level;
$S_G$ Rate at which glucose enter the blood due to food consumption;
$S_I$ Insulin injection term; and
$b_j$ Various parameters from relevant literature (e.g., $b_4$ may measure insulin sensitivity).
Given the following constraints:
1. All parameters and variables >0.
2. min($S_{G,I}$)=0.
3. A factor enforcing that $S_{G,I}$ be considered "sparse."
With the definition of an auxiliary variable (X) as $$X = \frac{b_6}{b_5} \int_{-\infty}^{t} G(s) e^{(s-t)/b_5} ds, \tag{Eq. 3}$$

the integro-differential equation specifies in equations 1-2 can be transformed into a simple third-order ordinary differential equation.

$$\frac{dX}{dt} = \frac{b_6}{b_5} G - \frac{1}{b_5} X \tag{Eq. 4}$$

$$\frac{dI}{dt} = -b_2 I + X + S. \tag{Eq. 5}$$

The equilibrium solution to equations 4-5 is:

$$\tilde{G} = \frac{-b_1 + \sqrt{b_1^2 + 4 b_4 b_6 b_7 / b_2}}{2 b_4 b_6 / b_2} \tag{Eq. 6}$$

-continued $$\tilde{I} = b_6 \tilde{G}/b_2 \qquad \text{(Eq. 7)}$$

$$\tilde{X} = b_6 \tilde{G}. \qquad \text{(Eq. 8)}$$

As noted above, the model module 214 can apply the statistical model to the explicit data values to impute one or more data values for the physiological state of the subject. For example, if the physiological data 222 includes explicit data values specifying the blood glucose level of the subject over a first time interval, then the model module 214 can impute data values for the blood glucose level of the subject over a second time interval.

The analytics module 216 can perform one or more analytic processes based on explicit data values and/or imputed data values. In some embodiments, the analytics module 216 performs an analytic process using a specific window of explicit data values and/or imputed data values corresponding to a glycemic event, a certain time interval (e.g., morning, afternoon, evening, or night), etc. Such action may be performed selectively. For instance, the analytics module 216 may only perform the analytic process(es) responsive to discovering the explicit data values and/or the imputed data values are indicative of bad glycemic health, good glycemic health, a downward trend in glycemic health, an upward trend in glycemic health, etc. Examples of analytic processes include generating post-glycemic event reports, prioritizing recommendations provided for improving the glycemic health state of the subject, examining glucose-related metrics critical in guiding diabetes treatment in a personalized manner, filtering certain data values from the physiological data 222 that are not to be examined by the excursion detection module 210, etc.

Thus, the analytics module 216 may parse the explicit data values to determine the glycemic health state of the subject. Similarly, the analytics module 216 may parse the imputed data values to predict the future glycemic health state of the subject. Such action may permit the analytics module 216 to identify whether the imputed data values are similar to, or dissimilar from, a target data series corresponding to a healthy glycemic state. The target data series may be a baseline representing the blood glucose levels and the glycemic responses considered to be normal by the American Diabetes Association (ADA). The target data series may correspond to the actual blood glucose measurements of an individual without diabetes. Alternatively, the target data series may be fabricated based on the glycemic range known to be indicative of a healthy glycemic state. Thus, the analytics module 216 can estimate the future glycemic state of the subject based on explicit data values previously generated by a glucose monitoring device.

After acquiring a stream of data values (e.g., explicit data values or imputed data values) indicative of the blood glucose level of a subject, the sensor management module 218 can configure the measurement schedule of a sensor capable of generating measurements in a dimension other than blood glucose. For example, the sensor management module 218 may configure the measurement schedule based on a glycemic event discovered in a stream of explicit data values or a predicted glycemic event discovered in a stream of imputed data values. Such action may result in a change to the resolution of the sensor, the polling frequency of the sensor, or any combination thereof. The sensor could be configured to monitor, for example, temperature, humidity, light, movement (e.g., acceleration), position (e.g., elevation or tilt), heart rate, blood pressure, etc. Thus, the sensor management module 218 may be responsible for managing a sensor designed to monitor a physiologic characteristic (also referred to as a "measurement dimension") other than blood glucose based on blood glucose measurements.

Imputing Data Values

Figure 3:
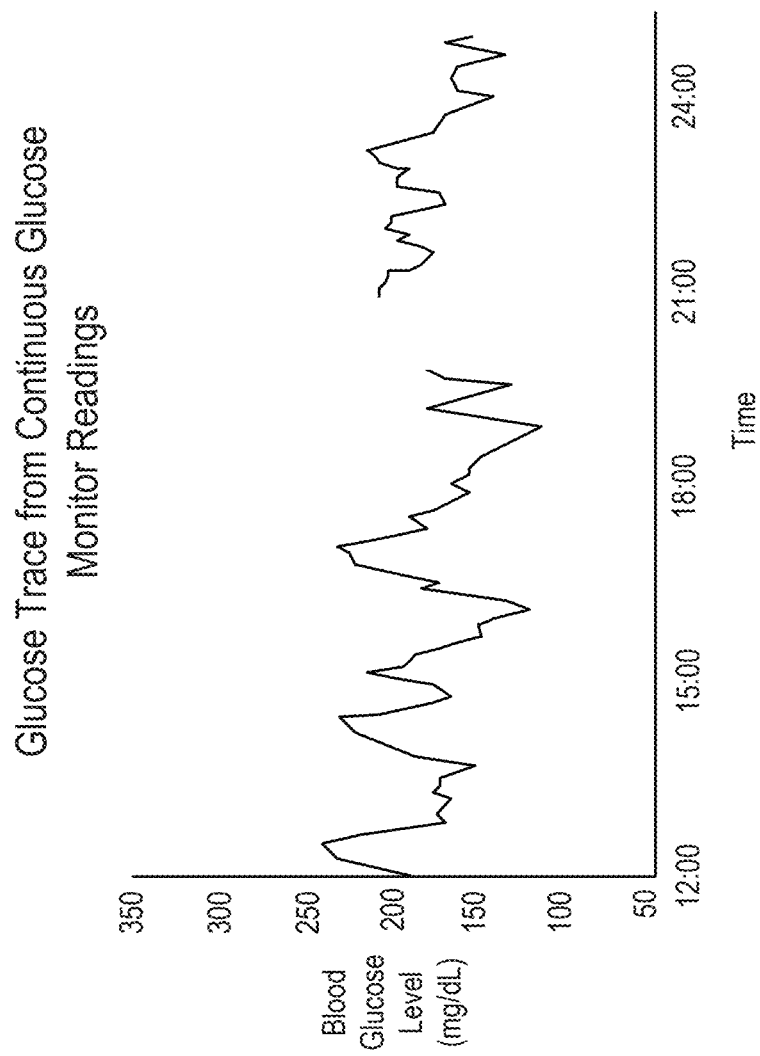
FIG. 3 depicts a glucose trace constructed from a series of measurements generated by a continuous glucose monitor over the course of a 12-hour period.

Visualizations can be helpful in conveying the importance of blood glucose level variations detected by glucose monitoring devices. One example is a glucose trace constructed from a series of measurements generated by a continuous glucose monitor over the course of a 12-hour period, as shown in FIG. 3. Glucose traces enable individuals to readily observe how consumption of a certain foodstuff or performance of a certain activity affects blood glucose level. However, glucose traces can be difficult to qualitatively interpret, even for professional diabetes educators and health coaches responsible for monitoring the glycemic health of individuals with diabetes (also referred to as "subjects" or "patients").

Figure 4:
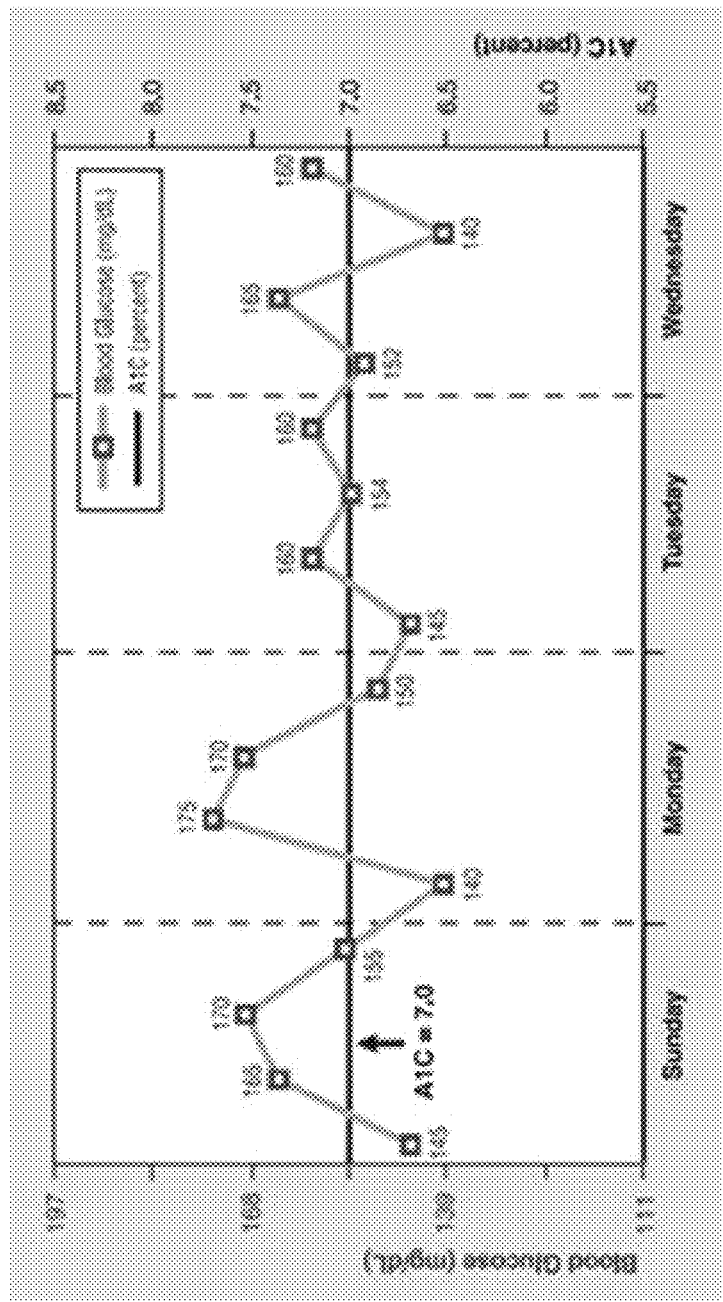
FIG. 4 depicts a series of measurements generated during administrations of A1c test over the course of several days.

Another example is a glucose trace constructed from a series of measurements generated by a blood glucose meter during sequential administrations of an A1c test, as shown in FIG. 4. The A1c test provides information about the average blood glucose level of a subject. The A1c test may also be referred to as the hemoglobin A1c, HbA1c, or glycohemoglobin test. FIG. 4 depicts a series of measurements generated during administrations of A1c test over the course of several days. The blood glucose level will increase following the ingestion of a foodstuff and then steadily decrease thereafter. Foodstuffs having a high glycemic index are more rapidly digested, and thus cause substantial fluctuations in the blood glucose level over a short period of time.

However, because the glucose trace shown in FIG. 4 is based on static glucose measurements generated by a blood glucose meter, the glucose trace can be misleading. For example, past glucose measurements are not necessarily indicative of future glucose measurements. Therefore, direct comparisons of previous time intervals (e.g., consecutive days) are often inaccurate or improper. Moreover, sporadic glucose measurements can make it difficult to draw meaningful conclusions for a time interval. For example, variations in the blood glucose level can easily be overestimated, underestimated, or missed entirely if the subject only performs the A1c test three or four times per day.

Introduced here are computer programs and associated computer-implemented techniques for imputing glucose measurements based on explicit glucose measurements generated by a glucose monitoring device, such as a blood glucose meter or a continuous glucose monitor. More specifically, a diabetes management platform can enable an intelligent design of a personalized statistical model (also referred to as an "imputation model") for imputing data values for the blood glucose level of a subject.

Figure 5:
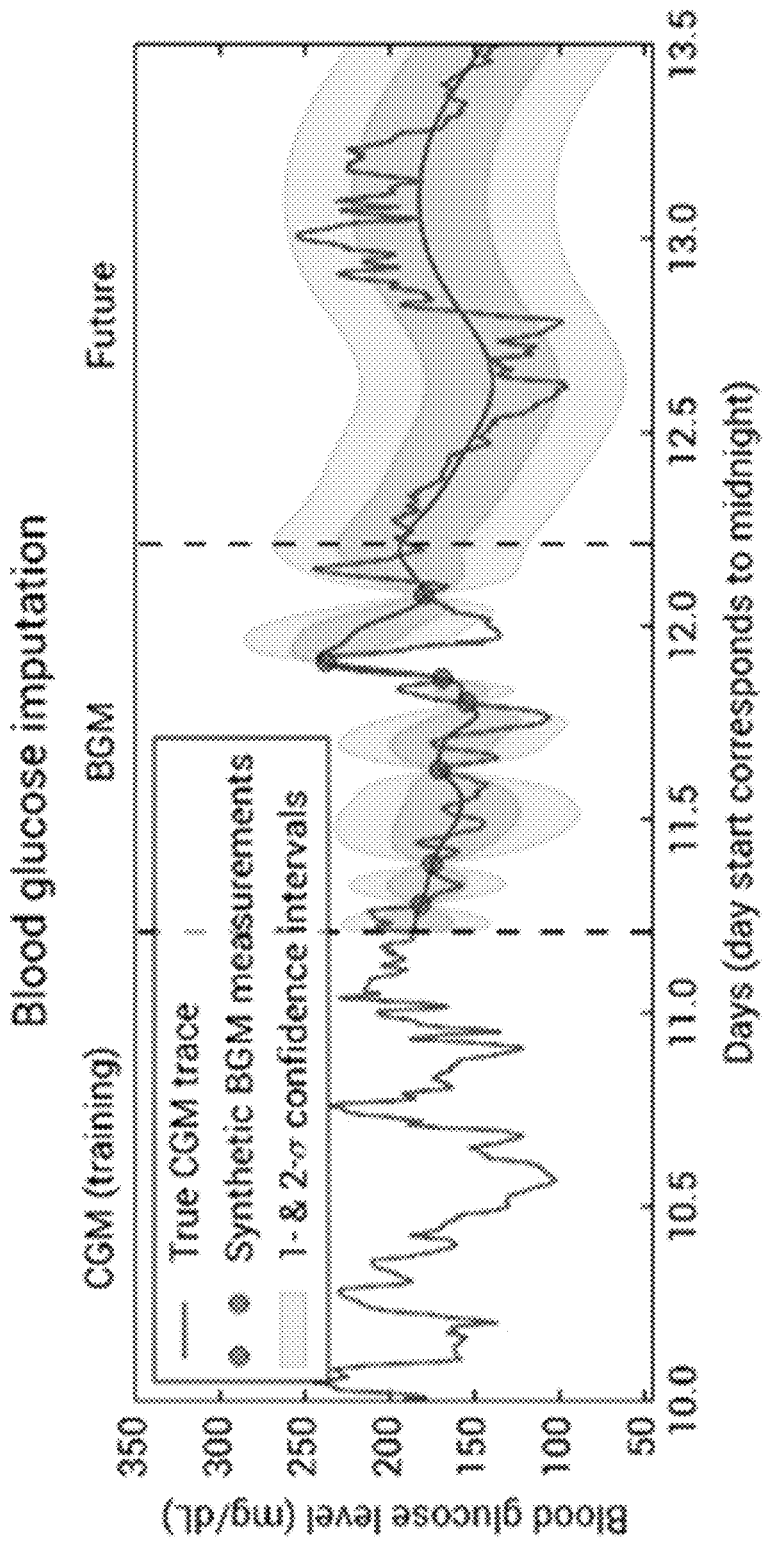
FIG. 5 illustrates how the diabetes management platform can design a statistical model for imputing future glucose measurements based on a first set of explicit glucose measurements included in training data.

FIG. 5 illustrates how the diabetes management platform can design a statistical model for imputing future glucose measurements based on a first set of explicit glucose measurements included in training data. An imputation model has been trained to fit 11 days of physiological data to the left of the first dashed vertical line. Here, the imputation model has also been fed 7 synthetic data values in the spirit of ad hoc measurements generated by a blood glucose meter. The gray confidence intervals illustrate where the imputation model believes subsequent data values are likely to reside.

In between the synthetic data values, the imputation model can interpolate the blood glucose level. Consequently, the uncertainty (e.g., represented as the width of the confidence intervals) may increase as the distance from the nearest synthetic data value increases. Outside of the region where these synthetic measurements exist, the imputation model can retreat to previously observed patterns (e.g., daily or weekly patterns).

In general, the diabetes management platform can initially examine explicit glucose measurements during a training period. The glucose monitoring device may be a continuous glucose monitor or a blood glucose meter. Here, for example, the first set of explicit glucose measurements is generated by a continuous glucose monitor. However, those skilled in the art will recognize that the first set of explicit glucose measurements could additionally or alternatively include values generated by a blood glucose meter.

The diabetes management platform may also consider a second set of explicit glucose measurements included in training data. Here, for example, the second set of explicit glucose measurements is generated by a blood glucose meter (BGM) on an ad hoc basis. These explicit glucose measurements are labeled as synthetic BGM measurements in FIG. 5. The diabetes management platform may use the second set of explicit glucose measurements to refine the statistical model, improve the accuracy of imputed glucose measurements, etc. In some instances, the diabetes management platform only examines a single set of explicit glucose measurements (e.g., either the first set of explicit glucose measurements or the second set of explicit glucose measurements) when designing the statistical model.

Each set of explicit glucose measurements may be associated with a different time interval. For example, the first set of explicit glucose measurements may correspond to a first time interval and the second set of explicit glucose measurements may correspond to a second time interval. These time intervals may be directly adjacent to one another as shown in FIG. 5.

The diabetes management platform can use the explicit glucose measurements to impute glucose measurements for a future time interval. For example, the diabetes management platform may examine imputed glucose measurements associated with a past time interval to impute glucose measurements for a future time interval. As another example, the diabetes management platform may examine explicit glucose measurements generated by a blood glucose meter, and then create a visualization of imputed glucose measurement(s) for review by an individual. The individual may be the subject whose blood glucose level is being monitored or a health coach responsible for monitoring the blood glucose level of the subject.

Figure 6A:
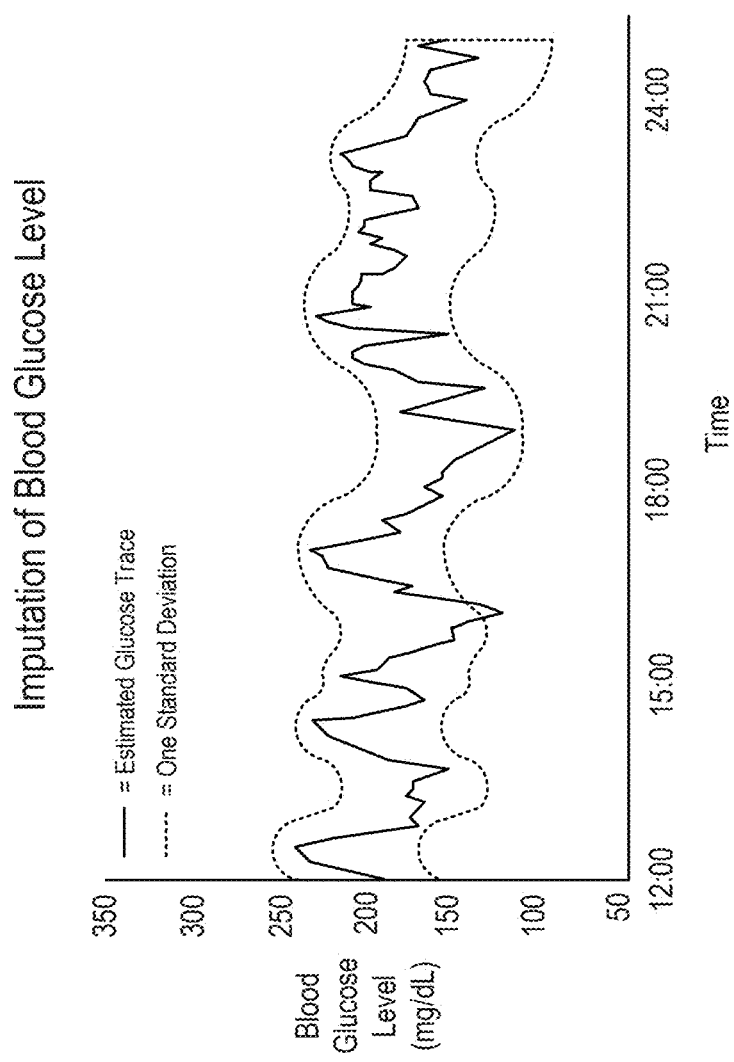
FIG. 6A depicts a visualization that includes a glucose trace and a single error bar.

In some embodiments, the visualization specifies the predicted blood glucose level at a specific time (e.g., "The blood glucose level is expected to be approximately 180 mg/dL at 12 PM."). In other embodiments, the visualization is a glucose trace that is indicative of an approximation of continuous monitoring of the blood glucose level. Thus, the glucose trace based on the imputed glucose measurement(s) may predictively mimic continuous monitoring by a continuous glucose monitor. The visualization may also include a bar plot showing the estimated blood glucose level of a time interval during which the subject hasn't yet taken an explicit glucose measurement. The bar plot may include one or more error bars overlaying the glucose trace. These error bar(s), which can correspond to different confidence interval(s), visually illustrate where the diabetes management platform expects imputed data values to reside. FIG. 5, for example, includes a first error bar corresponding to a confidence interval of one standard deviation and a second error bar corresponding to a confidence interval of two standard deviations. FIG. 6A, meanwhile, includes a single error bar corresponding to a confidence interval of one standard deviation.

Generally, training of the statistical model occurs before execution of the imputation process. Training can be done in several different ways.

For example, the diabetes management platform may examine a dataset for an individual corresponding to a past time interval. In such embodiments, the diabetes management platform could train the statistical model on the dataset and then impute values for an upcoming time interval.

As another example, the diabetes management platform may examine a dataset for an individual that includes a first subset (e.g., for a morning time interval) and a second subset (e.g., for an evening time interval). In such embodiments, the diabetes management platform could train the statistical model on the first subset and then impute additional values for the first subset. Additionally or alternatively, the diabetes management platform could train the statistical model on the first subset and then impute additional values for the second subset.

As another example, the diabetes management platform may examine a first dataset for a first individual and a second dataset for a second individual. These individuals may share a characteristic in common, such as age, ethnicity, activity level, diabetes classification, etc. In such embodiments, the diabetes management platform could train the statistical model on the first dataset and then impute additional values for the second dataset. Because blood glucose level is often highly dependent on the characteristics/circumstances of the corresponding individual, this type of training process may be avoided in favor of more personalized training processes.

Figure 6B:
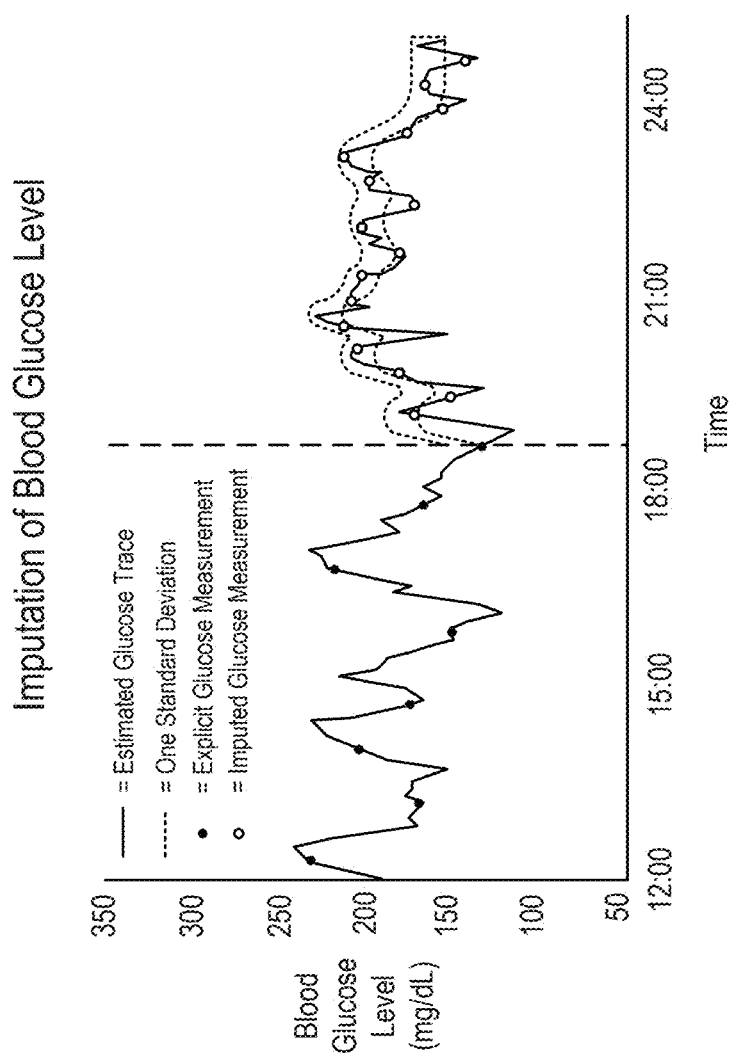
FIG. 6B depicts a visualization capable of being dynamically modified as new explicit data values are received.

FIG. 6B illustrates how the diabetes management platform may dynamically modify the bar plot as additional explicit glucose measurements are acquired over time. The diabetes management platform can, upon acquiring a new explicit glucose measurement, modify the bar plot to reflect the increase in certainty of the blood glucose level of the subject. For example, the diabetes management platform may monitor the duration since the most recent explicit glucose measurement. As the duration increases, the diabetes management platform may modify the bar plot by dynamically altering the width of the error bar(s). Increases in the width may be substantially proportional to increases in the duration.

Upon acquiring the new explicit glucose measurement, the diabetes management platform may replace a corresponding imputed glucose measurement with the new explicit glucose measurement. Generally, the corresponding imputed glucose measurement will be the closest past imputed glucose measurement. For example, if the diabetes management platform generates an imputed glucose measurement every half hour on the hour (e.g., 12:00, 12:30, 13:00, etc.), then an explicit glucose measurement taken at 12:55 will correspond to the imputed glucose measurement at 12:30. An explicit glucose measurement may correspond to multiple imputed glucose measurements if the time since the last explicit glucose measurements exceeds the periodicity of the imputed glucose measurements.

In some embodiments, imputed glucose measurements are visually distinguishable from explicit glucose measurements. In other embodiments, only imputed glucose measurements or explicit glucose measurements may be visible. For example, a visualization may include a visual representation of each explicit glucose measurement and an estimated glucose trace indicative of the imputed glucose measurements.

The diabetes management platform may also dynamically collapse the error bar(s) to indicate an increase in certainty of the blood glucose level due to the acquisition of the new explicit glucose measurement. Such action can incentivize subjects to administer the A1c test more frequently, thereby providing health coaches with more data to use when coaching the subjects. These techniques can be used in addition to, or instead of, conventional incentive techniques (e.g., affirmative messages and graphical illustrations of balloons/confetti/etc.).

Those skilled in the art will recognize that some individuals may prefer to see a mix of explicit and imputed glucose measurements (as shown in FIG. 6B), while other individuals may prefer to see only imputed glucose measurements for upcoming time intervals (as shown in FIG. 6A).

Figure 7:
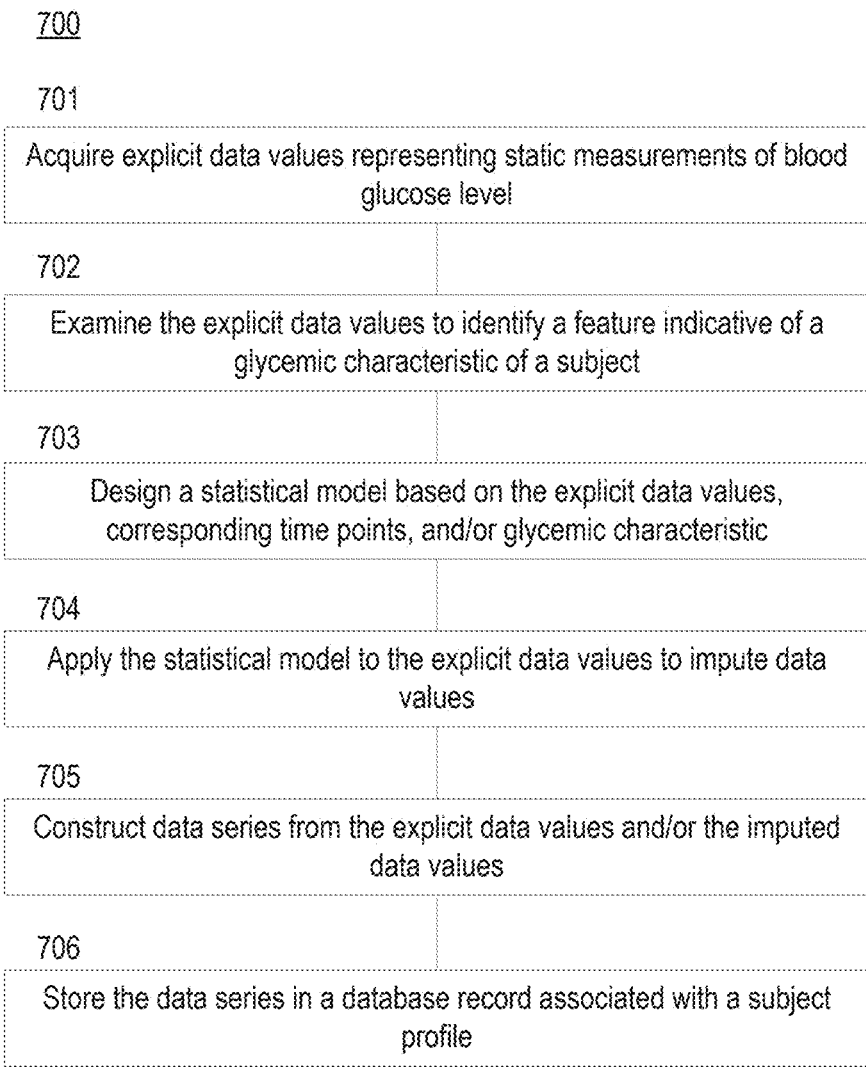
FIG. 7 depicts a flow diagram of a process for producing a statistical model for probabilistically imputing data values where explicit data values have not been generated.

FIG. 7 depicts a flow diagram of a process 700 for producing a statistical model for probabilistically imputing data values where explicit data values have not been generated. These imputed data values may be used to guide an individual toward a healthier glycemic state. For example, a diabetes management platform may examine the imputed data values to discover whether they are indicative of healthy or unhealthy blood glucose measurements. Such action may permit the diabetes management platform to recommend certain actions be performed or refrained from during an upcoming time interval.

Initially, the diabetes management platform acquires multiple explicit data values representing static measurements of the blood glucose level of a subject (step 701). Each explicit data value may correspond to a different time point. Thus, the diabetes management platform may construct a data series from the explicit data values that includes discrete, digitally-represented values in a temporal order that are indicative of time-varying glucose concentration sampled on an ad hoc basis.

The diabetes management platform can then examine the explicit data values to identify a feature indicative of a glycemic characteristic of the subject (step 702). The glycemic characteristic may be, for example, diabetes classification, blood glucose level trend(s) over certain time period(s), periodicity of the explicit data values, maximum data value, minimum data value, etc. The diabetes management platform can design a statistical model based on the explicit data values, the corresponding time points, the glycemic characteristic, or any combination thereof (step 703).

For example, the statistical model may be a Gaussian process model. In such embodiments, the diabetes management platform can create a radial basis kernel that indicates the blood glucose level is more likely to vary over long time intervals (e.g., hours) than short time intervals (e.g., seconds) and a periodic kernel that ensures any imputed data values conform with a periodic pattern of past explicit data values. The periodic pattern may be based on a series of past explicit data values taken over the course of a day, week, month, etc.

As another example, the statistical model may be a Kalman filtering model. In such embodiments, the diabetes management platform can, for each imputed data value, produce an estimated value indicative of the predicted blood glucose level at a future time, generate a variance measure indicative of the uncertainty of the estimated value, and periodically update the estimated value or the variance measure using a state transition model. The state transition model can be based on ordinary differential equation(s) representing the relevant biological responses. In some embodiments the ordinary differential equation(s) are adaptively personalized based on biological characteristic(s) of the subject, while in other embodiments the ordinary differential equation(s) are statically programmed based on biological literature.

The diabetes management platform can then apply the statistical model to the explicit data values to impute one or more data values for a future time interval where explicit data values have not been generated (step 704). Such action may require the diabetes management platform perform interpolation and/or extrapolation. Thus, for each imputed data value, the diabetes management platform can either interpolate the imputed data value from at least one explicit data value located within a certain proximity or extrapolate the imputed data value from a periodic pattern responsive to a determination that no explicit data values exist within the certain proximity. The certain proximity may be automatically determined by the diabetes management platform and/or manually specified by an individual. The certain proximity could be 30 minutes, 1 hour, 2 hours, 4 hours, etc.

Thus, the diabetes management platform may interpolate the blood glucose level between explicit data values taken on an ad hoc basis and extrapolate blood glucose level where no explicit data values exist. For example, if a Gaussian process is used for imputation, then the diabetes management platform can use as a kernel the sum of a Matern kernel and a periodic kernel. The periodic kernel may have a fixed period of 24 hours to capture/learn daily patterns of the subject. In some instances, a statistical model may revert to previously observed daily patterns due to enforcement of a 1-day-periodicity Gaussian process kernel. A series of imputed data values can include both interpolated data values and extrapolated data values.

In some embodiments, the diabetes management platform constructs a data series that includes the explicit data values and/or the imputed data values (step 705). The data series may be indicative of an approximation of continuous monitoring of the time-varying blood glucose level of the subject. The diabetes management platform may also store the explicit and imputed data values in separate data series. Thus, the explicit data values may be stored in a first data series and the imputed data values may be stored in a second data series. The diabetes management platform can store the data series in a database record associated with a subject profile (step 706). Additionally or alternatively, the diabetes management platform may store certain explicit/imputed data values in the subject profile. For example, the diabetes management platform may track the maximum value and/or the minimum value within a certain timeframe (e.g., a day, week, or month) or across the subject's entire history with the diabetes management platform. As another example, the diabetes management platform may track mean glucose, which could be updated over time as additional explicit data values are acquired.

Figure 8:
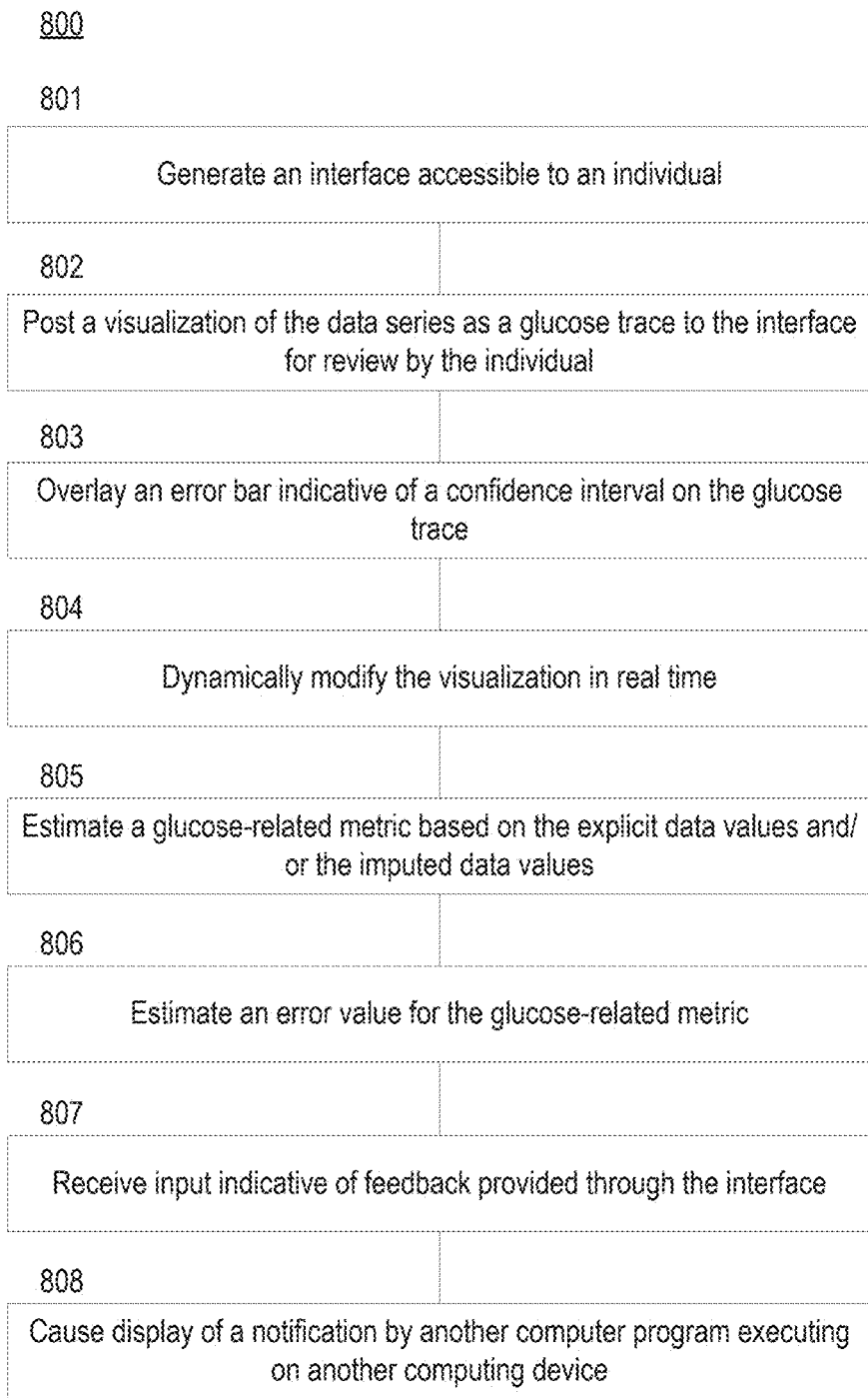
FIG. 8 depicts a flow diagram of a process for communicating the results of the process of FIG. 7 to an individual.

FIG. 8 depicts a flow diagram of a process 800 for communicating the results of process 700 to an individual. In some embodiments the individual is a person with diabetes, while in other embodiments the individual is interested in examining physiological data associated with some other person. Thus, the individual may be a health coach such as a medical professional (e.g., a physician or nurse), a diabetic health counselor, a family member, etc.

Initially, a computer program executing on a computing device will generate an interface accessible to an individual (step 801). The computer program can then post a visualization of the data series as a glucose trace over time to the interface for review by the individual (step 802). The visualization can take several different forms. For example, FIG. 5 depicts a visualization that includes a glucose trace and multiple error bars corresponding to different confidence intervals. As another example, FIG. 6A depicts a visualization that includes a glucose trace and a single error bar. As another example, FIG. 6B depicts a visualization capable of being dynamically modified as new explicit data values are received.

As noted above, the computer program may overlay an error bar indicative of a confidence interval on the glucose trace (step 803). The error bar may correspond to one standard deviation, two standard deviations, etc. In some embodiments, the error bar is one of multiple error bars corresponding to different confidence intervals (e.g., 1-σ confidence interval, 2-σ confidence interval, etc.).

In some embodiments, the computer program is configured to dynamically modify the visualization in real time (step 804). For example, upon acquiring a new explicit data value, the computer program may collapse the error bar to indicate an increase in the certainty of the time-varying blood glucose level due to the new explicit data value. As another example, the computer program may monitor the duration since the most recent explicit data value was received, and then modify the visualization based on the duration. More specifically, the computer program can adaptively alter the width of the error bar. Generally, the width of the error bar will increase as the duration increases (and thus confidence decreases) and decrease as the duration decreases (and thus confidence increases).

The computer program can estimate a glucose-related metric based on the explicit data values and/or the imputed data values (step 805). Examples of glucose-related metrics include time-in-range, mean glucose, day-estimated A1c level, standard deviation of the blood glucose level, coefficient of variation of the blood glucose level, etc. The computer program may post the glucose-related metric to the interface for review by the individual, store the glucose-related in a database record associated with a subject profile, etc.

In some embodiments, the computer program also estimates an error value for the glucose-related metric (step 806). The error value can also be posted to the interface for review by the individual, stored in the database record associated with the subject profile, etc.

If the individual is a health coach responsible for monitoring the glycemic health of another person (also referred to as a "subject" or "patient"), then the computer program may receive input indicative of feedback provided through the interface (step 807). The feedback may include a recommendation for improving the subject's glycemic health. For example, the health coach may identify certain activities or foodstuffs that are associated with a decline in glycemic health, and thus should be avoided. As another example, the health coach may identify certain activities or foodstuffs that are associated with an improvement in glycemic health, and thus should be performed. In such embodiments, the computer program may cause display of a notification by another computer program executing on another computing device associated with the subject (step 808). For example, the computer program may communicate directly with the other computer program through a simple messaging technology. As another example, the computer program may transmit the notification to a diabetes management platform, which may be responsible for forwarding the notification to the other computer program.

Other steps may also be performed. For example, if the individual is the subject whose blood glucose level is being monitored, then the computer program may automatically display a recommendation for improving the glycemic health state. Thus, the recommendation may not be based on feedback provided by a health coach. Instead, the computer program could dynamically identify appropriate feedback based on the explicit data values and/or the imputed data values. As another example, the computer program may determine an accuracy measure for the statistical model upon acquiring a new explicit data value. The accuracy measure may be discovered by comparing the new explicit data value to a corresponding imputed data value. The computer program may alter the statistical model responsive to a determination that the accuracy measure falls below a threshold.

The computer program may also enable a health coach to perform other action(s). For example, the health coach may be able to make an annotation that is dynamically linked to an explicit data value or an imputed data value. Generally, the annotation is subsequently presented to the subject for review. However, the annotation may not be shown to the subject (e.g., in instances where the health coach flags an imputed data value to be examined more closely for accuracy). As another example, the health coach may be able to generate a comparison of the imputed data values and the explicit data values corresponding to the same interval. The comparison can permit the health coach to visually observe accuracy in estimating the blood glucose level over time.

Moreover, the computer program may enable the health coach to compile visualization component(s) using the explicit data values, the imputed data values, etc. The visualization component(s) could include text, audio, video, or any combination thereof. Some visualization components only include text specifying a recommendation for improving glycemic health, while other visualization components include audio and/or video for incentivizing future performance of certain activities (e.g., compliance with a testing regimen may be incentivized by showing digital balloons, confetti, etc.). As another example, the computer program may identify actual trends in the blood glucose level by examining the explicit data values. Such trends may indicate whether the glycemic health of the subject is improving or declining over time. Similarly, the computer program may identify predicted trends in the blood glucose level by examining the imputed data values. Such trends may indicate whether the glycemic health of the subject is expected to improve or decline over time.

These steps described above may be performed in various sequences and combinations. For example, the diabetes management platform may simultaneously notify a subject whose blood glucose level is being monitored and a health coach responsible for monitoring the glycemic health of the subject. As another example, the diabetes management platform may periodically execute these processes such that imputed data values are generated on a periodic basis (e.g., daily, weekly, or monthly).

Other steps may also be included in some embodiments. For example, the diabetes management platform may perform an analytic process on the explicit data values and/or the imputed data values to estimate the glycemic health state of the subject. Such action may be performed selectively. For instance, the diabetes management platform may only perform the analytic process responsive to discovering the imputed data values are indicative of bad/good glycemic health. Examples of analytic processes include prioritizing recommendations provided for improving the glycemic state of the subject, examining glucose-related metrics critical in guiding diabetes treatment in a personalized manner, posting certain glucose-related metrics and/or visualizations to an interface for review by the subject or a health coach, etc.

Additional information on imputing data values based on explicit data values generated by a glucose monitoring device can be found in U.S. application Ser. No. 16/249,633, which is incorporated herein by reference in its entirety.

Discovering Excursions in Physiological Data

As noted above, a diabetes management platform may impute data values based on explicit data values representative of discrete measurements of the blood glucose level of a subject. These imputed data values may allow the diabetes management platform to better understand the blood glucose level during a past time interval (e.g., in between a set of explicit data values) or a future time interval (e.g., following the explicit data values). Accordingly, the diabetes management platform may use the imputed data values to predict which glycemic events, if any, are likely to be experienced by the subject during the future time interval.

Introduced here are computer programs and associated computer-implemented techniques for discovering excursions in the physiological data of a subject whose glycemic health state is being monitored and then characterizing the excursions. More specifically, a diabetes management platform can apply rule set(s) to the physiological data to discover glycemic events, propose therapeutic behavior changes, etc. Thus, the diabetes management platform can automatically surface reminders regarding certain actions, interesting glycemic characteristics (e.g., the blood glucose level was abnormally low upon waking or abnormally high during the evening), etc. The diabetes management platform can provide these insights instead of, or in addition to, those offered by health coaches.

By classifying excursions detected in the physiological data, the diabetes management platform can facilitate the identification of a therapeutic behavior change intended to improve the glycemic health state of the subject. For example, a health coach may review the glycemic event(s) associated with a subject before generating a recommendation for improving the glycemic health state. As another example, the diabetes management platform may automatically generate a recommendation for improving the glycemic health state based on characteristics of the excursion(s), such as duration, frequency, intensity, etc. As another example, the diabetes management platform may examine data generated by a sensor capable of generating measurements in a dimension other than blood glucose to discover what relationship, if any, exists between blood glucose and the other dimension.

Figure 9:
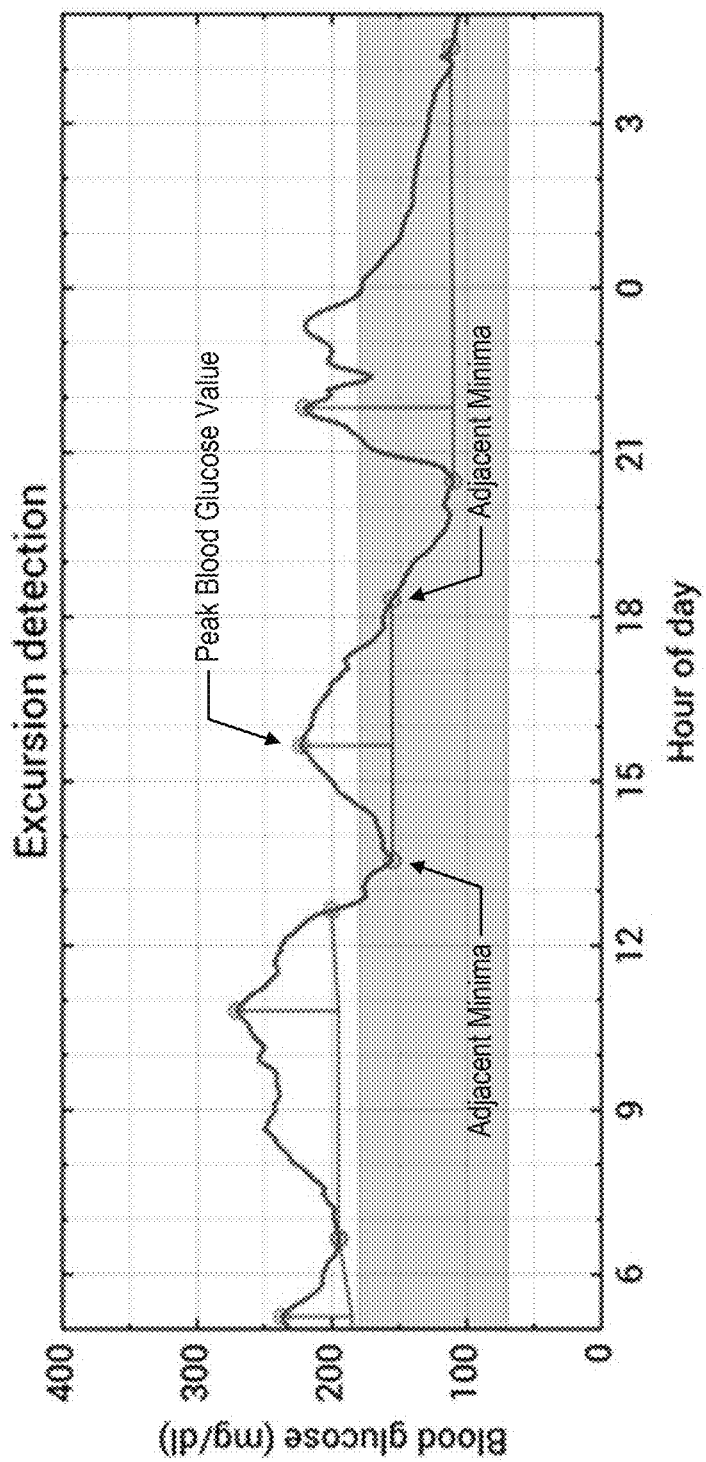
FIG. 9 illustrates how the diabetes management platform can apply processing algorithm(s) to physiological data detect excursions in the blood glucose level.

FIG. 9 illustrates how the diabetes management platform can apply processing algorithm(s) to physiological data detect excursions in the blood glucose level. As noted above, the physiological data can include explicit data values and/or imputed data values. An excursion is a variation in the blood glucose level exceeding a specified amount within a predetermined time interval. Generally, the variation will be a positive variation (e.g., due to consumption of a foodstuff), though the variation could also be a negative variation. In some embodiments excursions are detected based only on a time series of blood glucose level values, while in other embodiments excursions are detected based on other information in addition to the time series of blood glucose level values. The other information may include metadata, user input, other signals (e.g., from a glucose monitoring device, fitness tracker, mobile phone, etc.), etc. The diabetes management platform may also apply other processing algorithm(s) to detect excursions caused by other types of glycemic events. For example, some embodiments of the diabetes management platform examine the glycemic recovery following meals due to, for example, performance of an exercise activity.

By applying the processing algorithm(s), the diabetes management platform can detect semi-global minima over a configurable time interval. Thus, the diabetes management platform may find the time interval boundaries that permit the blood glucose level to be a global minimum within a surrounding time interval. In some embodiments the time intervals are manually defined by an individual, while in other embodiments the time intervals are automatically defined by the diabetes management platform. For example, the diabetes management platform may set the time intervals to match a natural rhythm/cycle, such as a circadian cycle, menstrual cycle, feeding cycle, elimination cycle, etc.

The diabetes management platform can then pair adjacent minima and ensure that a sufficiently large excursion occurs in between the adjacent minima. An excursion may be sufficiently large if the peak blood glucose value exceeds an upper threshold, if the difference between the peak blood glucose value and the adjacent minima exceeds a certain amount, etc. Additionally or alternatively, the excursion may be defined based on the relationship between the adjacent minima and/or the peak blood glucose value and the glycemic range recommended by the ADA. Thus, the processing algorithm(s) can include two parameters (i.e., a pair of semi-global minima and a peak value) that are fit to physiological data generated by a glucose monitoring device. While embodiments may be described in the context of semi-global minima associated with an upward excursion, the technology is similarly applicable to downward excursions. In contrast to upward excursions, downward excursions are defined by a pair of semi-global maxima and a minimal value.

Several different heuristics and/or algorithms can be implemented by the diabetes management platform to discover excursions. For example, given a time series of continuous glucose monitoring data, the diabetes management platform may detect all relative minima over windows of a certain timescale (e.g., 30 minutes, 60 minutes, 120 minutes, etc.). The diabetes management platform can pair successive minima into candidate excursion intervals, and then refine the candidate excursion intervals using one or more criteria. For example, the diabetes management platform may prevent an excursion interval from ending at a blood glucose level lower than where the excursion interval began. Moreover, the diabetes management platform may filter candidate excursion intervals having a height smaller than a certain amount (e.g., 10 mg/dL, 20 mg/dL, 30 mg/dL, etc.). These parameters (e.g., the certain timescale and the certain amount) may be personalized over time based on characteristics of the subject, such as recovery rate, average blood glucose value, etc.

In some embodiments, the diabetes management platform identifies excursions by applying patterns to detect matching parameter(s). The diabetes management platform may be communicatively coupled to a library of patterns corresponding to different glycemic events. For example, the library may include patterns that allow the diabetes management to readily identify instances of hypoglycemia, pre-sleep meals, administrations of medication, etc.

Figure 10:
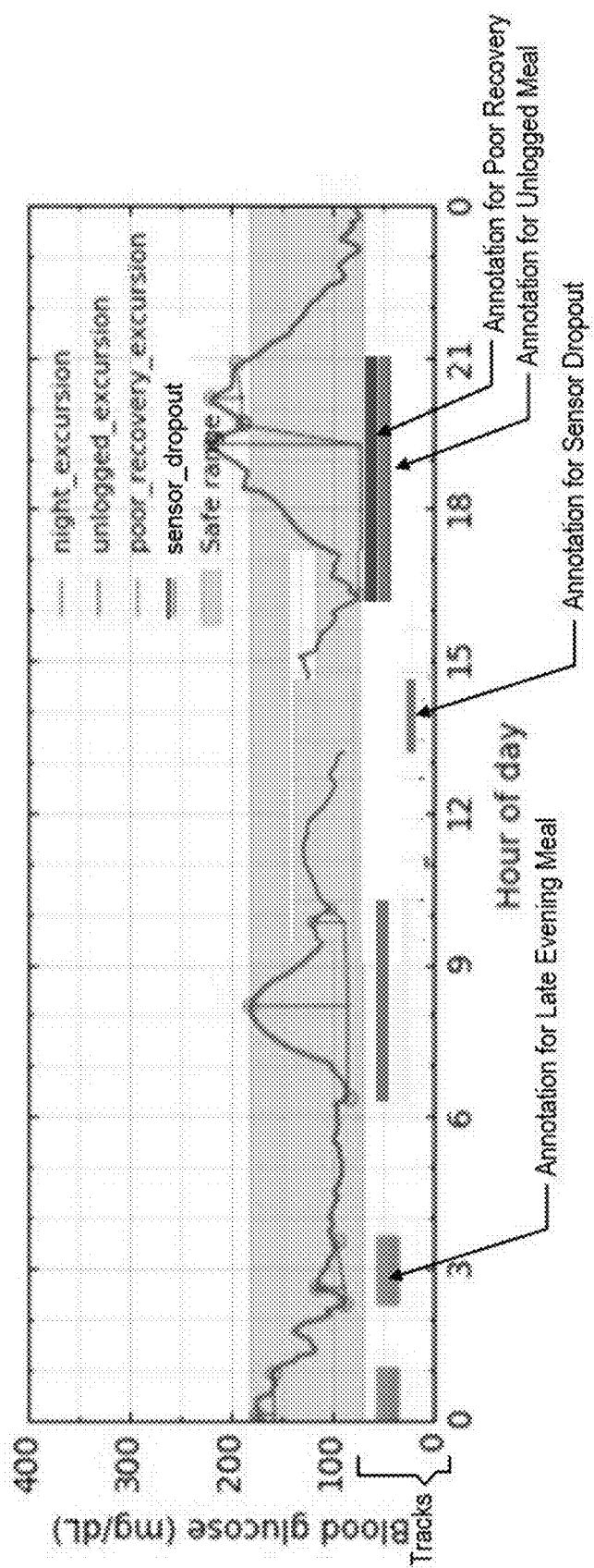
FIG. 10 illustrates how the diabetes management platform can automatically classify a variety of signal features indicative of different glycemic events.

FIG. 10 illustrates how the diabetes management platform can automatically classify a variety of signal features indicative of different glycemic events. Examples of glycemic events include:

Meals that are unrelated to any subject-logged meals catalogued in a database. Often, a subject will manually log meals through a computer program associated with the diabetes management platform. The diabetes management platform may identify excursions that don't match a corresponding logged meal (e.g., through the comparison of time metadata derived from, or included with, the physiological data to records of logged meals).

Meals that are associated with an abnormally quick glycemic recovery (e.g., a glycemic recovery exceeding an upper rate) or an abnormally slow glycemic recovery (e.g., a glycemic recovery falling below a lower rate).

Meals that will cause the blood glucose level to exceed an upper threshold following consumption of the next meal. These meals will cause the blood glucose level to enter an unsafe glycemic range following the next meal.

Meals that occur within a certain proximity of a temporal event (e.g., a sleep cycle). For example, the diabetes management platform may detect meals that are consumed by subjects late in the evening to avoid having blood glucose level drop too low during the night. Because these events can be associated with medication problems, they provide a clear intervention point.

Meals that are substantially dissimilar from other meals in a nearby time interval (e.g., occurring in the same day or week), occurring at a similar time (e.g., occurring around the same time on consecutive days), etc. In some embodiments dissimilar meals are "bad" meals surrounded by "good" meals, while in other embodiments dissimilar meals are "good" meals surrounding by "bad" meals. A "bad" meal will generally cause the blood glucose level to exceed the upper threshold of the glycemic range recommended by the ADA. A "good" meal, meanwhile, will generally cause the blood glucose level to remain within the glycemic range recommended by the ADA.

Periodic patterns in the blood glucose value. For example, the diabetes management platform may detect that a subject struggled to stay within the recommended glycemic range during certain time periods (e.g., mornings, afternoons, evenings, or nights). Moreover, the diabetes management platform can infer information about the corresponding meals (i.e., breakfast, lunch, dinner, or sporadic snacks) based on the certain time periods.

Blood glucose values exceeding an upper threshold (e.g., 180 mg/dL, 200 mg/dL, 225 mg/dL, etc.).

Blood glucose values falling below a lower threshold (e.g., 60 mg/dL, 80 mg/dL, 100 mg/dL, etc.).

Time intervals corresponding to glucose monitoring device-related issues. Examples of such issues include sensor dropout, faulty excursion data values, etc. The diabetes management platform may detect when sensor dropouts occur from gaps in physiological data. Sensor dropouts may be an indicator of poor placement/fit, replacement, etc.

Hypoglycemic events. Some glucose monitoring devices can generate hypoglycemia alerts based on a direct comparison of the blood glucose level to one or more thresholds. For example, some glucose monitoring devices generate alerts upon detecting blood glucose levels below a predefined threshold (e.g., 55 ml/dL) and a user-defined threshold (e.g., 70 mg/dL). However, the diabetes management platform may also be able to detect trends/instances of near hypoglycemia without necessarily triggering an alert. For example, the diabetes management platform may detect that a subject consistently has a low blood glucose level (e.g., 75 mg/dL) in the early morning hours (e.g., around 3:00 AM). Although the diabetes management platform may not generate an alert specifying a hypoglycemic event occurred, the diabetes management platform may notify a health coach of such behavior.

FIG. 10 depicts an example of a visualization that includes two annotations corresponding to unlogged meals, two annotations corresponding to late evening meals, one annotation corresponding to an instance of poor glycemic recovery, and one annotation corresponding to a sensor dropout. Each annotation (also referred to as a "label") is associated with a corresponding time interval, whose duration is defined by the at least one pair of adjacent minima used to define the excursion. In some instances, a glycemic event may be defined by multiple excursions. Here, for example, a single annotation is used to represent the unlogged meal that occurred around 4:30 PM. Annotations may also partially or entirely overlap one another. Here, for example, the annotation corresponding to the instance of poor glycemic recovery covers the same time interval as one of the annotations corresponding an unlogged meal.

Generally, sensor dropouts correspond to time intervals in which no physiological data has been acquired by the diabetes management platform. For example, physiological data may not be generated when the glucose monitoring device is replaced (e.g., on a weekly basis), the glucose monitoring device is dislodged (e.g., comes loose from the skin due to poor placement, loose tape, etc.), etc. As another example, physiological data may not be available if the communication channel between the glucose monitoring device and the computing device on which the diabetes management platform resides is disrupted. In such scenarios, the missing physiological data may not backfill if the glucose monitoring device is configured to stream physiological data to the computing device in real time.

As shown in FIG. 10, the visualization may also depict the glycemic range recommended by the ADA. Here, the recommended glycemic range of 80 mg/dL to 180 mg/dL is highlighted gray. However, the upper threshold (i.e., 180 mg/dL) and the lower threshold (i.e., 80 mg/dL) could also be depicted using horizontal lines (e.g., solid, dashed, or dotted lines).

Additionally or alternatively, other glycemic ranges may be depicted in a visualization. For example, a subject whose blood glucose level is being monitored may be associated with a healthcare regimen that is intended to guide the subject toward a healthier glycemic range. In such embodiments, the glycemic range depicted in the visualization may change over time. Thus, the glycemic range may be 120-220 mg/dL during a first time interval, 100-200 mg/dL during a second time interval, etc. Gradual shifts in the glycemic range can facilitate improvement in the glycemic health state of the subject in a manner more susceptible to behavior change (e.g., because the subject can readily examine their blood glucose level with respect to the changing glycemic range).

Annotations of different types may be arranged along separate tracks positioned beneath the glucose trace. The separate tracks enable the diabetes management platform to depict multiple annotations that are easily distinguishable from one another, yet still temporally aligned. Thus, the separate tracks enable the diabetes management platform to easily classify a time interval as being indicative of multiple glycemic events (and thus multiple annotations). Here, for example, the time interval from 4-9 PM is associated with an annotation corresponding to an instance of poor glycemic recovery and an annotation corresponding to an unlogged meal. Annotations of different types may also be visually distinguishable from one another. For example, in some embodiments each type of annotation is associated with a different color, while in other embodiments each type of annotation is associated with a different line type (e.g., solid, dashed, dotted, etc.).

In some embodiments, annotations are also used to identify physiological data values that require further examination/analysis. For example, if a subject sleeps on a glucose monitoring device, then the data values generated by the glucose monitoring device may be artificially low due to poor readings. Because the diabetes management platform can readily determine that these low data values are not indicative of the true blood glucose level (e.g., by comparing to previous nights or monitoring a trend in the blood glucose level throughout the day), the diabetes management platform can identify the corresponding time interval as being a candidate for further analysis.

FIG. 11 depicts a flow diagram of a process 1100 for discovering signal features in physiological data specifying the blood glucose level of a subject whose glycemic health state is being monitored. By examining these signal features, a diabetes management platform can classify excursions detected in the physiological data to facilitate the identification of a therapeutic behavior change to be performed by the subject to improve the glycemic health state.

Initially, a diabetes management platform acquires physiological data (step 1101). Generally, the physiological data includes a series of static measurements of the blood glucose level of the subject. Thus, the physiological data may include discrete, digitally represented values in a temporal order that are indicative of time-varying glucose concentration as sampled on a periodic or ad hoc basis. In some embodiments, the physiological data also includes imputed measurements generated by the diabetes management platform (e.g., based on the series of static measurements).

The diabetes management platform can then post a visualization of the physiological data as a glucose trace over time to an interface for review by an individual (step 1102). In some embodiments the individual is a person with diabetes, while in other embodiments the individual is interested in examining physiological data associated with some other person. Thus, the individual may be a health coach such as a medical professional (e.g., a physician or nurse), a diabetic health counselor, a family member, etc. FIG. 10 depicts an example of a glucose trace that is based on explicit measurements generated by a continuous glucose monitor. However, a glucose trace could be based on explicit measurements, imputed measurements, or any combination thereof.

The diabetes management platform may also examine the physiological data to detect an excursion in the blood glucose level of the subject (step 1103). By parsing the physiological data, the diabetes management platform can detect a signal feature defined by one or more data values. Examples of signal features include the minimum blood glucose value, the maximum blood glucose value (also referred to as the "peak blood glucose value"), the total area beneath the peak blood glucose value (i.e., an integral of a glucose trace over the duration of the peak blood glucose value), a recovery rate following the peak blood glucose value, a time characteristic of the minimum or peak blood glucose values, etc. Thus, while some excursions may be defined by blood glucose level variations exceeding a specified amount, other excursions may be based on the magnitude of a single data value (e.g., in the case of the minimum and peak blood glucose values).

Several different techniques can be employed for detecting excursions in the blood glucose level of the subject. In some embodiments, the diabetes management platform detects an excursion that exceeds a specific threshold, selects a time interval that includes the excursion, and classifies, in response to selecting the time interval, the data value(s) defining the excursion as being indicative of a glycemic event. In other embodiments, the diabetes management platform segments the physiological data into multiple time intervals, classifies each time interval of the multiple time intervals based on the presence of any glycemic events, merges consecutive time intervals having the same classification, and identifies, from both the merged and unmerged time intervals, a time interval corresponding to a certain glycemic event. Accordingly, the multiple time intervals examined by the diabetes management time intervals may include both merged and unmerged time intervals (e.g., consecutive time intervals having the same classification are a subset of the multiple time intervals). Thus, the time interval under consideration may be a single time interval or a combined time interval formed from more than one of the multiple time intervals.

The diabetes management platform can then classify the excursion as being indicative of a glycemic event (step 1104). The term "glycemic event" broadly refers to any event that affects the blood glucose level. Examples of such events include the performance of an exercise activity, consumption of a foodstuff, administration of a medication, etc. Thus, the diabetes management platform may determine that an upward variation in the blood glucose level exceeding a certain amount likely corresponds to consumption of a foodstuff. Similarly, the diabetes management platform may determine that a downward variation in the blood glucose level exceeding a certain amount likely correspond to administration of a medication. In some embodiments, the diabetes management platform can detect characteristic(s) of the glycemic event based on feature(s) of the excursion. For example, if the upward variation in the blood glucose level exceeds a certain threshold, then the diabetes management platform may determine that the subject likely consumed a large meal or a meal high in carbohydrates. Examples of such excursion features include the total variation in the blood glucose level, duration of the excursion, maximum/minimum values, etc.

The diabetes management platform can also identify an annotation corresponding to the glycemic event (step 1105). For example, responsive to classifying the excursion as being indicative of a glycemic event, the diabetes management platform may designate an annotation for a target time period based on the glycemic event. In some embodiments, the target time period is the same as the time interval over which the signal feature is present. In other embodiments, the target time period is a subset of the time interval over which the signal feature is present. Said another way, the time interval may be a superset of the target time period. For example, the time interval may include an onset period preceding the annotated glycemic event and/or a tail period following the annotated glycemic event.

The diabetes management platform can then cause display of the annotation on the interface for review by the individual (step 1106). As shown in FIG. 10, the diabetes management platform can represent the annotation as a horizontal line arranged beneath a corresponding window of physiological data represented as a glucose trace. The glucose trace and the annotation can be aligned with respect to a common time axis, thereby visually alerting the individual of potential changes in the glycemic health state of the subject.

The diabetes management platform will often characterize continuous windows of physiological data with different annotation(s). As shown in FIG. 10, a visualization can include multiple annotations. Moreover, because an excursion may be indicative of multiple types of glycemic events, the diabetes management platform may overlay multiple annotations on top of one another (e.g., by arranging each annotation along a separate track beneath the glucose trace). Visual presentation of these annotations can facilitate the discovery of the glycemic health state of the subject, the recommendation of a therapeutic behavior change for improving the glycemic health state, the identification of comparable subjects and/or glycemic events, etc.

In some embodiments, the diabetes management platform further stores an indication of the annotation in a database to create a historical record of annotations associated with the subject (step 1107). Because each annotation is associated with a glycemic event, the historical record of annotations can also represent a historical record of glycemic events experienced by the subject. More specifically, the diabetes management platform can configure a subject profile in the database to specify that the glycemic event occurred at a certain time. Thus, the subject profile can include an entry for each glycemic event, a time interval during which the glycemic event occurred, etc. In some embodiments the time interval is dynamically generated (e.g., by identifying a start time corresponding to initiation of the excursion and an end time corresponding to conclusion of the excursion), while in other embodiments the time interval is selected from a predetermined list (e.g., by determining whether the glycemic event occurred during the morning, afternoon, evening, or night).

When the annotations are stored in the database, the diabetes management platform can perform various operations. For example, the diabetes management platform may receive input indicative of a request to identify similar instance(s). Thus, a health coach may ask to see instances where the subject experienced hypoglycemia, a blood glucose level exceeding 100 mg/dL during the night, a sensor dropout, etc. Moreover, the diabetes management platform may perform browsing/filtering of the historical record of annotations. Thus, a health coach may ask to see instances where the subject concurrently experienced two different glycemic events. These features are particularly useful for health coaches who are responsible for reviewing large sets of physiological data (e.g., for hundreds of subjects or over hundreds of days).

Figure 12:
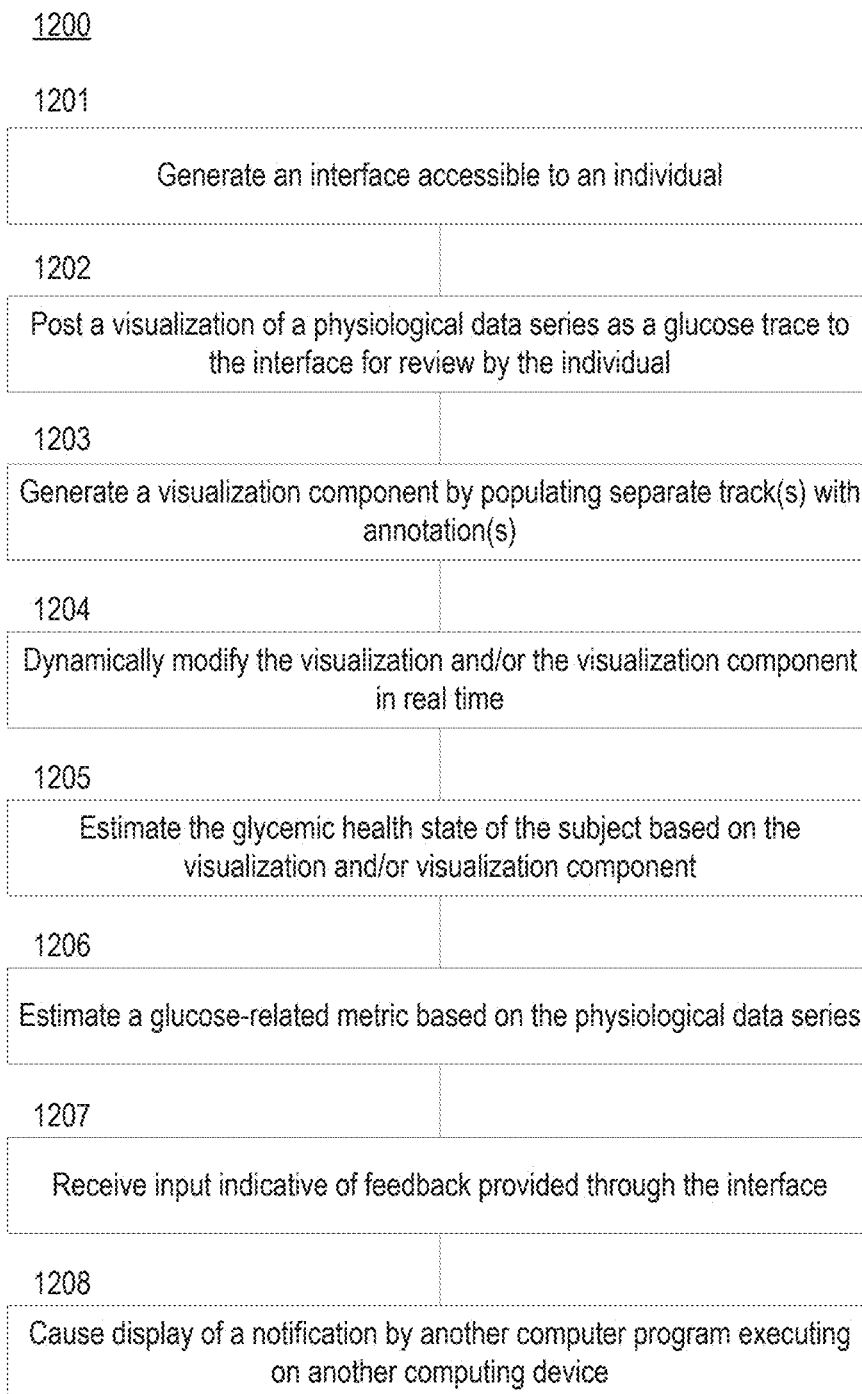
FIG. 12 depicts a flow diagram of a process for facilitating the acquisition of feedback from an individual for improving the glycemic health state of a subject whose blood glucose level is being monitored.

FIG. 12 depicts a flow diagram of a process 1200 for facilitating the acquisition of feedback from an individual for improving the glycemic health state of a subject whose blood glucose level is being monitored. As noted above, the individual may be the subject or some other person, such as a health coach responsible for monitoring the glycemic health state of the subject.

Initially, a computer program executing on a computing device will generate an interface accessible to an individual (step 1201). The computer program can then post a visualization of physiological data as a glucose trace to the interface for review by the individual (step 1202). The visualization can take several different forms. FIG. 10 depicts an example of a glucose generated over an interval of time.

The computer program can then compile a visualization component that identifies excursions in the physiological data that represent glycemic events. More specifically, the computer program can populate one or more tracks arranged alongside the glucose trace with one or more annotations (step 1203). Generally, the track(s) are located beneath the glucose trace. However, the track(s) could be located above the glucose trace. Moreover, the computer program may overlay the track(s) on the glucose trace, in which case the annotations may appear when the individual hovers over the corresponding window of the glucose trace.

While separate tracks are useful when multiple annotations are associated with a single time interval, other visualization components can also be compiled. For example, the computer program may generate text-based annotations that label specific time intervals. As another example, the computer program may distinguish certain time intervals using vertical lines (e.g., solid, dashed, or dotted lines) or shaded segments to identify individual excursions.

In some embodiments, the computer program is configured to dynamically modify the visualization and/or the visualization component in real time (step 1204). For example, upon acquiring new physiological data, the computer program can modify the glucose trace to indicate that new information is available regarding the time-varying blood glucose level. As another example, the computer program may automatically begin examining new physiological data to identify excursions in the physiological data. Thus, the computer program may identify glycemic events represented by excursions in the physiological data, as well as predict which glycemic event(s) are likely to occur in the future based on patterns in the physiological data. For example, the computer program may determine that if the blood glucose level falls below a lower threshold, then the subject is likely to overconsume at their next meal. In such a scenario, the computer program may proactively notify the subject that they should be mindful of how much food is being consumed and/or notify the health coach to provoke proactive coaching before an unhealthy glycemic health state is reached.

The computer program can estimate a glycemic health state of the subject based on the visualization and/or the visualization component (step 1205). The glycemic health state may be based on the annotation and/or other characteristics of the excursion, such as duration, frequency, intensity, etc. For example, the computer program may apply a rule set that specifies the number of annotations within a time interval (e.g., a 24-hour period matching a circadian cycle) is inversely proportional to the glycemic health state. Generally, the more annotations within a time interval, the more likely the subject is in a "bad" glycemic health state.

The computer program can also estimate a glucose-related metric based on the physiological data series (step 1206). Examples of glucose-related metrics include time-in-range, mean glucose, day-estimated A1c level, standard deviation of the blood glucose level, coefficient of variation of the blood glucose level, etc. The computer program may post the glucose-related metric to the interface for review by the individual, store the glucose-related metric in a database record associated with a subject profile, etc.

If the individual is a health coach responsible for monitoring the glycemic health of another person (also referred to as a "subject" or "patient"), then the computer program may receive input indicative of feedback provided through the interface (step 1207). The feedback may include a recommendation of a therapeutic behavior change intended to improve the subject's glycemic health state. For example, the health coach may identify certain activities or foodstuffs that are associated with a decline in glycemic health, and thus should be avoided. As another example, the health coach may identify certain activities or foodstuffs that are associated with an improvement in glycemic health, and thus should be performed. In such embodiments, the computer program may cause display of a notification by another computer program executing on another computing device associated with the subject (step 1208). For example, the computer program may communicate directly with the other computer program through a simple messaging technology. As another example, the computer program may transmit the notification to a diabetes management platform, which may be responsible for forwarding the notification to the other computer program.

Other steps may also be performed. For example, if the individual is the subject whose blood glucose level is being monitored, then the computer program may automatically display a recommendation for improving the glycemic health state. Thus, the recommendation may not be based on feedback provided by a health coach. Instead, the computer program could dynamically identify appropriate feedback based on the excursions, glycemic events, or annotations. As another example, the computer program may prioritize a pool of subjects for review by the health coach based on the number of annotations corresponding to each subject, the type of annotations corresponding to each subject, the level of subject involvement (e.g., based on the number of unlogged meals detected), etc. These criteria can be used to identify those subject(s) that are having the most difficulty maintaining a healthy glycemic state. Prioritization enables the health coach to provide feedback to those subjects who consistently struggle to maintain their glycemic health before those subjects who occasionally struggle to maintain their glycemic health.

Moreover, the computer program may enable the health coach to compile other visualization components based on the excursions, glycemic events, or annotations. These visualization components could include text, audio, video, or any combination thereof. Some visualization components only include text specifying a recommendation for improving glycemic health, while other visualization components include audio and/or video for incentivizing future performance of certain activities (e.g., logging meals may be incentivized by showing digital balloons, confetti, congratulatory messages, etc.).

These steps may be performed in various sequences and combinations. For example, the diabetes management platform may simultaneously notify a subject whose blood glucose level is being monitored and a health coach responsible for monitoring the glycemic health of the subject. As another example, the diabetes management platform may periodically execute these processes such that visualizations and annotations are generated on a periodic basis (e.g., daily, weekly, or monthly).

Other steps may also be included in some embodiments. For example, the diabetes management platform may perform an analytic process on physiological data to detect whether there are any time intervals in which the blood glucose measurements are rarely taken. Such action may be performed selectively. For instance, the diabetes management platform may only perform the analytic process responsive to discovering the physiological data was generated by a blood glucose meter that generates blood glucose measurements on an ad hoc basis. An annotation may be generated to identify these time intervals with sporadic coverage. Other examples of analytic processes include prioritizing recommendations provided for improving the glycemic health state of the subject, examining glucose-related metrics critical in guiding diabetes management in a personalized manner, posting certain glucose-related metrics and/or visualizations to an interface for review by the subject or a health coach, etc.

Additional information on discovering excursions in data values can be found in U.S. application Ser. No. 15/891,291, which is incorporated herein by reference in its entirety.

Managing Measurement Schedules of Sensors

As noted above, individuals with diabetes can benefit from gaining a better understanding of how their blood glucose level fluctuates throughout the day. However, it can be difficult to understand blood glucose level measurements, which represent a technical signal indicative of the diabetes disease state. To better understand the impact of glycemic events, some entities have begun examining the relationship between the blood glucose level and another physiological parameter, such as heart rate or blood pressure. However, this relationship can be difficult to understand, especially for physiological parameters that appear to be unrelated.

Introduced here are computer programs and associated computer-implemented techniques for discovering glycemic events in a series of data values representative of blood glucose measurements and then altering the measurement schedule of a sensor capable of generating measurements in a dimension other than blood glucose based on the glycemic events.

The sensor could be configured to monitor temperature, humidity, light, movement (e.g., acceleration), position (e.g., elevation or tilt), heart rate, blood pressure, etc. The sensor can be implemented in one or more stages. In a two-stage implementation, the sensor can include a raw-sensing sub-component (e.g., an accelerometer or a tilt sensor) and a computing unit (e.g., a processor). In such embodiments, the computing unit can infer physical activity from the measurements generated by the raw-sensing sub-component. For example, the computing unit may examine raw data representative of acceleration measurements generated by an accelerometer to determine when an individual slept. As another example, the computing unit may examine raw data representative of heart rate measurements generated by a heart rate monitor (e.g., that is included in a wearable electronic device) to determine when the individual slept. In these examples, the same physical activity is monitored even though the raw-sensing sub-components generate measurements in different dimensions. Additionally or alternatively, a diabetes management platform may infer physical activity from the measurements generated by the raw-sensing sub-component. In some embodiments, the sensor forwards raw data generated by the raw-sensing sub-component directly to the diabetes management platform for analysis (e.g., without examining the raw data). In other embodiments, the computing unit of the sensor examines the raw data to infer physical activity, and then the sensor forwards the raw data to the diabetes management platform for additional analysis.

Figure 13:
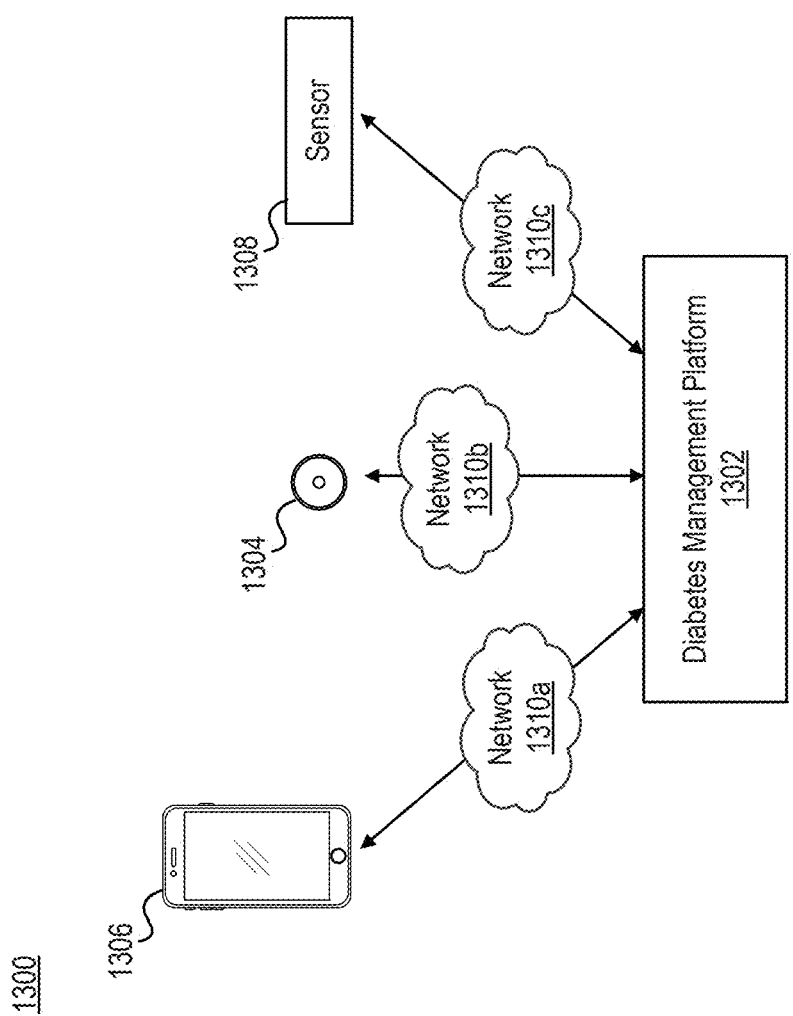
FIG. 13 depicts an example of a communication environment that includes a diabetes management platform configured to acquire data from, or send data to, one or more sources.

FIG. 13 depicts an example of a communication environment 1300 that includes a diabetes management platform 1302 configured to acquire data from, or send data to, one or more sources. Here, for example, the diabetes management platform 1302 is communicatively coupled to a glucose monitoring device 1304, a mobile phone 1306, and a sensor 1308 capable of generating measurements in a dimension other than blood glucose (collectively referred to as the "networked devices"). While the sensor 1308 is shown as a standalone component, those skilled in the art will recognize that the sensor 1308 may be part of a computing device. For example, the sensor 1308 may be housed within a wearable electronic device (e.g., a watch or fitness tracker) or the mobile phone 1306.

The networked devices can be connected to the diabetes management platform 1302 via one or more networks 1310a-c. The network(s) 504a-c can include PANs, LANs, WANs, MANs, cellular networks, the Internet, etc. Additionally or alternatively, the networked devices may communicate with one another over a short-range communication protocol, such as Bluetooth® or NFC. For example, the diabetes management platform 1302 resides on the mobile phone 1306 in some embodiments. In such embodiments, data received from the mobile phone 1306 need not traverse any networks. However, the mobile phone 1306 may be connected to the glucose monitoring device 1304 and/or the sensor 1308 via separate Bluetooth communication channels.

Embodiments of the communication environment 1300 may include some or all of the networked devices. For example, some embodiments of the communication environment 1300 include a diabetes management platform 1302 that receives explicit data values from the glucose monitoring device 1304. While a continuous glucose monitor is shown in FIG. 13, the glucose monitoring device 1304 could be a blood glucose meter. As noted above, the diabetes management platform 1302 may examine explicit data values generated by the glucose monitoring device 1304 and/or imputed data values generated by the diabetes management platform 1302 to discover excursions indicative of glycemic events. These excursions may be indicative of past glycemic events that have been experienced by a subject and/or future glycemic events that could be experienced by the subject.

Based on these excursions, the diabetes management platform 1302 can configure the measurement schedule of the sensor 1308. For example, the diabetes management platform 1302 may alter the resolution and/or the polling frequency of the sensor 1308 upon discovering an excursion representative of a given glycemic event. Such action may cause the resolution to be highest within a time interval corresponding to the peak value of the excursion. In some embodiments, the diabetes management platform may configure the measurement schedule such that the resolution gradually increases before the time interval and then gradually decreases following the time interval. If the excursion is at least partially defined by imputed data values, then the diabetes management platform 1302 can preemptively change the measurement schedule in advance of a predicted glycemic event.

The diabetes management platform can alter the measurement schedule of a sensor in at least two different scenarios.

Figure 14:
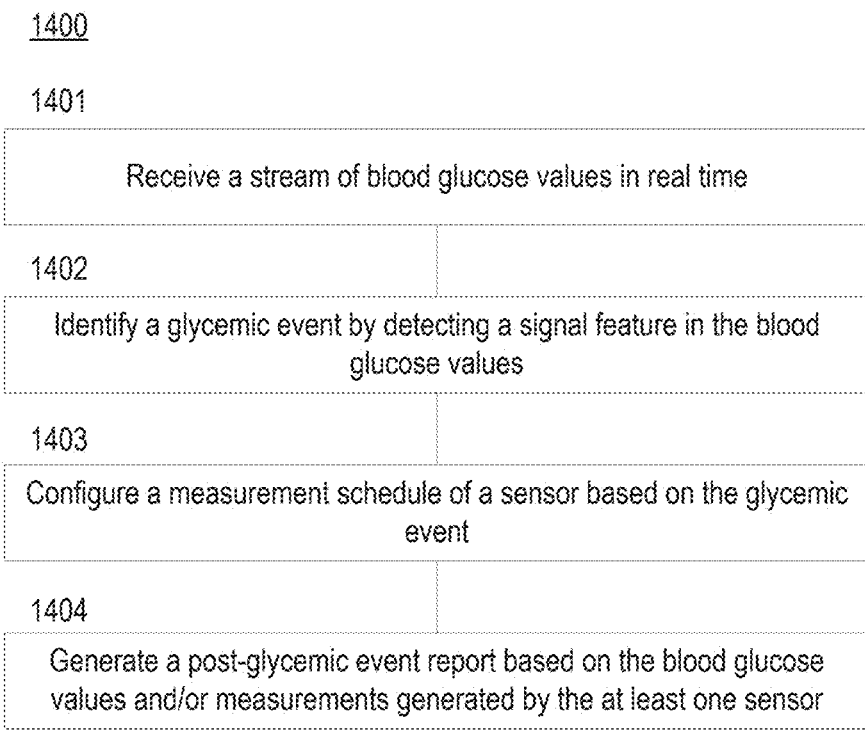
FIG. 14 depicts a flow diagram of a process for altering the measurement schedule of a sensor as part of a real-time investigation process.

First, the diabetes management platform may configure the measurement schedule as part of a real-time investigation process. FIG. 14 depicts a flow diagram of a process 1400 for altering the measurement schedule of a sensor as part of a real-time investigation process. Initially, a diabetes management platform can receive a stream of data values in real time (step 1401). The stream can include explicit data values generated by a glucose monitoring device and/or implicit data values generated by the diabetes management platform. For example, in some embodiments, the diabetes management platform may receive a substantially real-time data stream comprised entirely of imputed data values (also referred to as "estimated blood glucose values"). Thus, the diabetes management platform may receive imputed data values as those values are created, or the diabetes management platform may receive imputed data values corresponding to a future time interval of a given length (e.g., 30 seconds, 1 minute, 3 minutes, or 5 minutes). The future time interval may commence immediately (e.g., the diabetes management platform may receive a stream of imputed data values corresponding to the next 3 minutes).

The diabetes management platform can then identify a glycemic event by detecting a signal feature in the series of data values (step 1402). For example, the diabetes management platform may parse the series of data values to discover a signal feature defined by a pair of dynamically-determined, semi-global minima values and a peak value.

Thereafter, the diabetes management platform can configure a measurement schedule of the sensor based on the glycemic event (step 1403). Thus, the diabetes management platform may make adjustment(s) to the measurement schedule depending on what type of glycemic events, if any, are discovered in the series of data values. In some embodiments, these adjustment(s) are made responsive to (e.g., immediately following) the discovering of the glycemic event(s). By altering the measurement schedule of the sensor, the diabetes management platform can better understand how, if at all, dimensions other than blood glucose are related to the glycemic health state of a subject whose blood glucose level is being monitored. For example, the diabetes management platform may cause the resolution and/or polling frequency of the sensor to be highest within a predetermined interval of time expected to include a glycemic event. Such action enables the diabetes management platform to gain a better understanding of dimension(s) other than blood glucose level during intervals of time that are relevant to the glycemic health state, as well as conserve power by limiting measurements during intervals of time that are not relevant (or less relevant) to the glycemic health state.

In some embodiments, the diabetes management platform may simultaneously or sequentially configure the measurement schedules of multiple sensors based on the glycemic event. These sensors may be designed to monitor different measurement dimensions, and these measurement schedules may be configured independently of one another. Thus, the diabetes management platform may independently alter a first measurement schedule associated with a first sensor designed to measure acceleration, a second measurement schedule associated with a second sensor designed to measure heart rate, a third measurement schedule associated with a third sensor designed to measure skin temperature and/or ambient temperature, etc. For example, the diabetes management platform may increase the resolution of a first sensor designed to generate measurements in a first dimension and decrease the resolution of a second sensor designed to generate measurements in a second dimension. As another example, the diabetes management platform may increase or decrease the resolution of multiple sensors designed to generate measurements in the same dimension by different amounts.

After the glycemic event has occurred, the diabetes management platform may generate a post-glycemic event report based on the series of data values and/or the measurements generated by the sensor (step 1404). The post-glycemic event report may be made accessible to a health coach responsible for discovering what relationship, if any, exists between blood glucose and the other dimension measured by the sensor.

Figure 15:
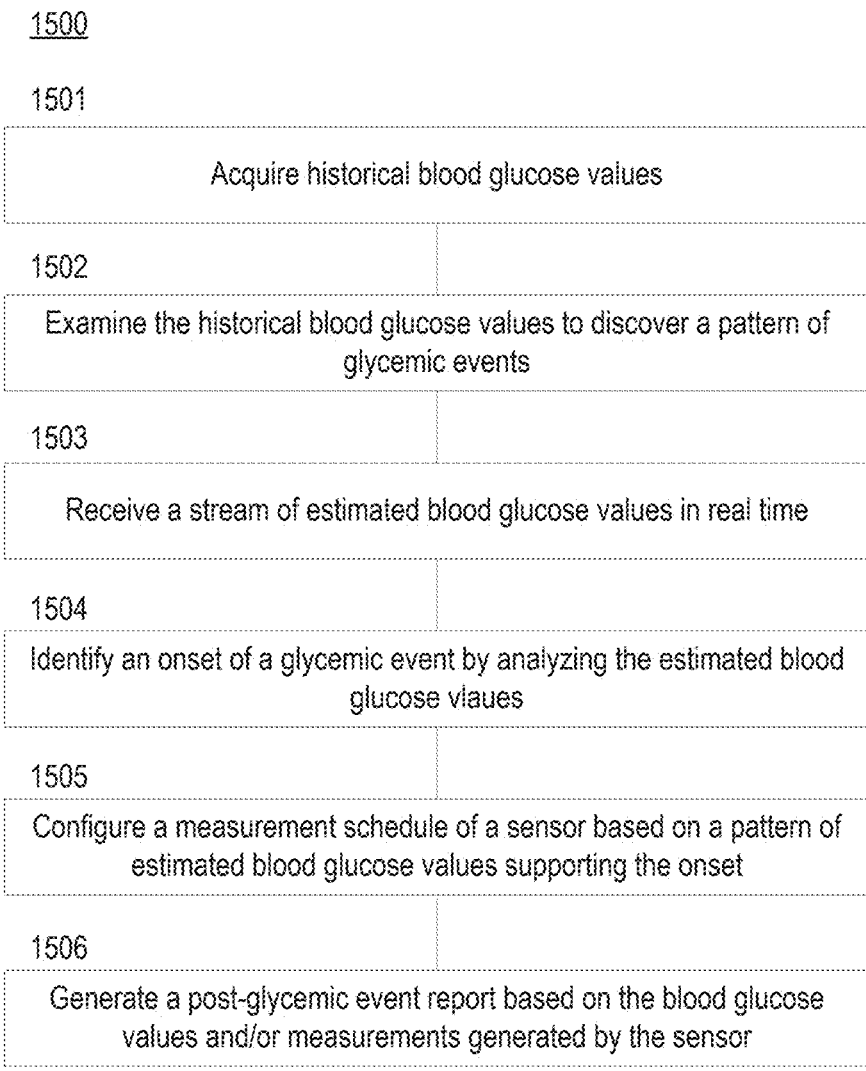
FIG. 15 depicts a flow diagram of a process for altering the measurement schedule of a sensor as part of a predictive investigation process.

Second, the diabetes management platform may configure the measurement schedule as part of a predictive investigation process. FIG. 15 depicts a flow diagram of a process 1500 for altering the measurement schedule of a sensor as part of a predictive investigation process. Initially, a diabetes management platform can acquire historical blood glucose values (step 1501). The historical blood glucose values may include explicit data values generated by a glucose monitoring device and/or implicit data values generated by the diabetes management platform. For example, in some embodiments, each historical blood glucose value is an implicit data value (also referred to as an "estimated data value"). Moreover, the historical blood glucose values may be associated with one or more individuals. For example, in some embodiments the historical blood glucose values are associated with a single individual, while in other embodiments the historical blood glucose values are associated with a cohort of individuals who share a characteristic in common.

The diabetes management platform can then examine the historical blood glucose values to discover a pattern of glycemic events (step 1502). Such action may enable the diabetes management platform to discover several patterns at different cadences. For example, the diabetes management platform may discover glycemic events that occur multiple times per day, once per day, multiple times per week, etc.

Thereafter, the diabetes management platform can receive a stream of imputed data values representative of blood glucose measurements in real time (step 1503). For example, the diabetes management platform may receive a substantially real-time data stream comprised entirely of imputed data values (also referred to as "estimated blood glucose values"). The diabetes management platform can then identify a potential onset of a glycemic event by analyzing the estimated blood glucose values (step 1504). The diabetes management platform may identify potential onsets of glycemic events based on the patterns of glycemic events discovered in the historical blood glucose values, as well as the signal features defining those glycemic events.

The diabetes management platform can then configure a measurement schedule of a sensor based on the pattern of estimated blood glucose values supporting the potential onset (step 1505). Step 1505 of FIG. 15 is substantially similar to step 1403 of FIG. 14. However, because the potential onset is based on estimated blood glucose values, the diabetes management platform can preemptively change the measurement schedule in advance of the glycemic event.

After the glycemic event has occurred, the diabetes management platform may generate a post-glycemic event report based on measurements generated by a glucose monitoring device and/or measurements generated by the sensor (step 1506). The post-glycemic event report may be made accessible to a health coach responsible for discovering what relationship, if any, exists between blood glucose and the other dimension measured by the sensor.

These steps may be performed in various sequences and combinations. For example, the diabetes management platform may simultaneously and independently configure the measurement schedules of multiple sensors. Other steps may also be included in some embodiments. For example, in some embodiments, the diabetes management platform may generate a notification for presentation on an electronic device associated with the individual for whom the onset is identified. The notification may specify the configured measurement schedule and prompt the individual to manually approve execution/implementation of the configured measurement schedule. Alternatively, the diabetes management platform may be configured to implement the configured measurement schedule on behalf of the individual without requiring user input.

Processing System

Figure 16:
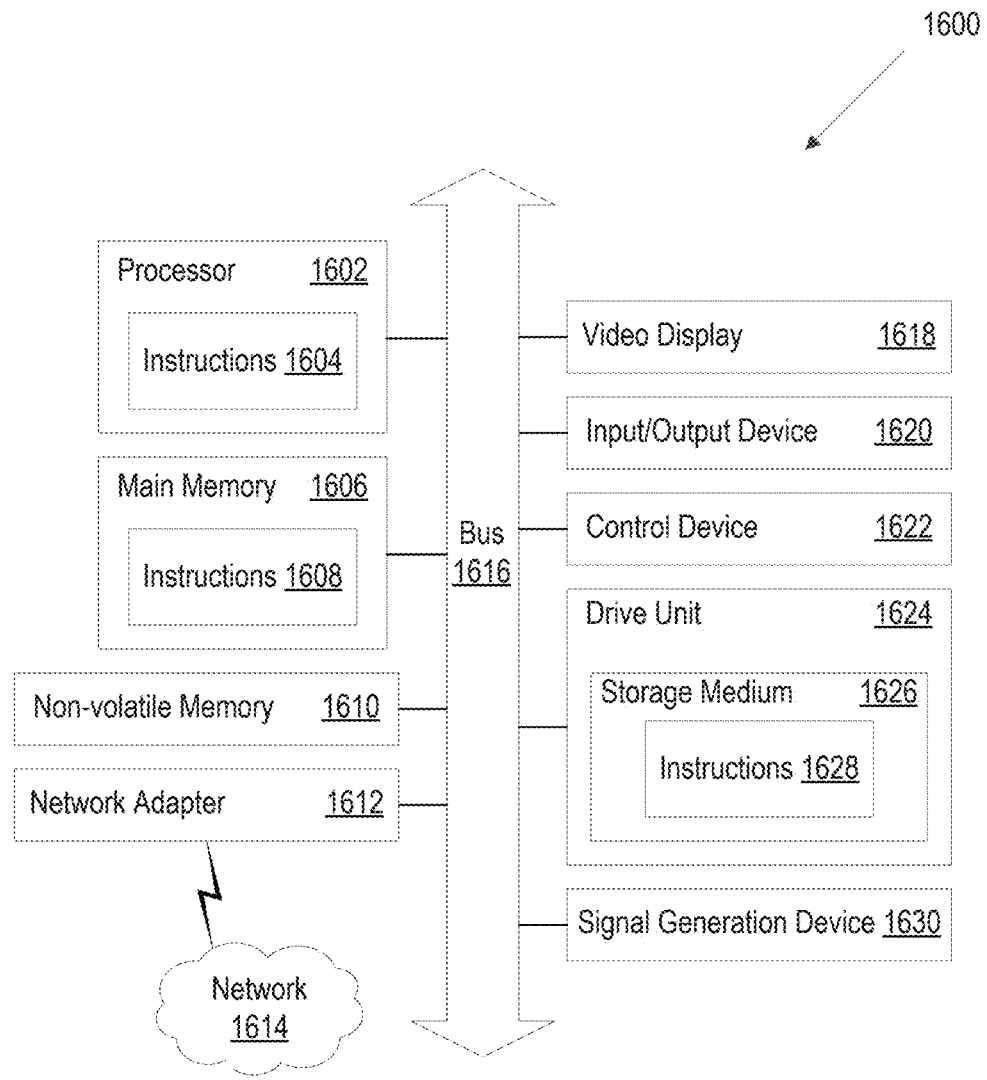
FIG. 16 is a block diagram illustrating an example of a processing system in which at least some operations described herein can be implemented.

FIG. 16 is a block diagram illustrating an example of a processing system 1600 in which at least some operations described herein can be implemented. For example, some components of the processing system 1600 may be hosted on a computing device that includes a diabetes management platform (e.g., diabetes management platform 102 of FIG. 1).

The processing system 1600 may include one or more central processing units ("processors") 1602, main memory 1606, non-volatile memory 1610, network adapter 1612 (e.g., network interface), video display 1618, input/output devices 1620, control device 1622 (e.g., keyboard and pointing devices), drive unit 1624 including a storage medium 1626, and signal generation device 1630 that are communicatively connected to a bus 1616. The bus 1616 is illustrated as an abstraction that represents one or more physical buses and/or point-to-point connections that are connected by appropriate bridges, adapters, or controllers. The bus 1616, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 1600 may share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the processing system 1600.

While the main memory 1606, non-volatile memory 1610, and storage medium 1626 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 1628. The term "machine-readable medium" and "storage medium" shall also be taken to include any medium that is capable of storing, encoding, or carrying a set of instructions for execution by the processing system 1600.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1604, 1608, 1628) set at various times in various memory and storage devices in a computing device. When read and executed by the one or more processors 1602, the instruction(s) cause the processing system 1600 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 1610, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 1612 enables the processing system 1600 to mediate data in a network 1614 with an entity that is external to the processing system 1600 through any communication protocol supported by the processing system 1600 and the external entity. The network adapter 1612 can include a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1612 may include a firewall that governs and/or manages permission to access/proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A non-transitory medium with instructions stored thereon that, when executed by a processor, cause the processor to perform operations comprising:
   identifying a potential instance of a glycemic event by
      applying, to a series of explicit values representative of discrete measurements of blood glucose of an individual, a model that produces a series of imputed values for the blood glucose of the individual, and
      parsing the series of explicit values and/or the series of imputed values to discover one or more values that are determined to be representative of the potential instance of the glycemic event; and
   altering, in response to said identifying, a measurement schedule of a sensor by increasing a frequency at which the sensor measures a physiological parameter other than blood glucose, so as to increase insight into the physiological parameter over an interval of time that corresponds to the potential instance of the glycemic event while conserving power during intervals of time that are less relevant to glycemic health of the individual.

2. The non-transitory medium of claim 1, wherein the series of explicit values is provided to the model as input, such that the series of imputed values is produced as output based on a statistical analysis of the series of explicit values.

3. The non-transitory medium of claim 1, wherein the one or more values are imputed values that are representative of an excursion that exceeds a predetermined amount.

4. The non-transitory medium of claim 1, wherein the operations further comprise:
   generating a notification for presentation to the individual for whom the potential instance of the glycemic event is identified.

5. The non-transitory medium of claim 4, wherein the notification specifies the measurement schedule, the execution of which requires at least some manual interaction by the individual.

6. The non-transitory medium of claim 1, wherein the processor is part of a computing device that is communicatively connected, via separate wireless communication channels, to the sensor and a glucose monitoring device that generates the series of explicit data values.

7. A method comprising:
   obtaining, by a processor,
      (i) a series of explicit values that are representative of actual measurements of a blood glucose level of an individual, and
      (ii) a series of imputed values that are represented of predicted measurements of the blood glucose level of the individual;
   detecting, by the processor, an instance of a glycemic event by examining the series of explicit values and the series of imputed values to discover one or more values that are determined to be representative of the instance of the glycemic event; and modulating, by the processor, a frequency with which a sensor generates one or more physical measurements for the individual in a measurement dimension other than blood glucose over an interval of time that corresponds to the instance of the glycemic event, so as to increase insight into the measurement dimension while conserving power during intervals of time that are less relevant to glycemic health of the individual.

8. The method of claim 7, wherein by modifying the frequency over the interval of time corresponding to the instance of the glycemic event, further insight is gained into the measurement dimension other than blood glucose before, during, or after the instance of the glycemic event.

9. The method of claim 7, wherein the one or more values are explicit values that are determined to be representative of the instance of the glycemic event.

10. The method of claim 7, wherein the one or more values are imputed values that are determined to be representative of the instance of the glycemic event.

11. The method of claim 7, wherein said modulating results in a gradual increase in the frequency before the interval of time corresponding to the glycemic event and a gradual decrease in the frequency after the interval of time.

12. The method of claim 7, wherein the sensor is configured to measure temperature, humidity, light, movement, position, heart rate, blood pressure, or any combination thereof.

13. The method of claim 7, further comprising:

generating, by the processor, a report based on (i) the series of explicit values, (ii) the series of imputed values, and (iii) the one or more physical measurements, so as to convey whether a relationship exists between blood glucose and the measurement dimension other than blood glucose.

14. A non-transitory medium with instructions stored thereon that, when executed by a processor, cause the processor to perform operations comprising:

examining a signal that is representative of discrete, digitally-represented measurements that are generated by a first sensor for a first physiological parameter and that are arranged in temporal order, so as to identify a variation in the first physiological parameter that corresponds to a change in health of an individual; and modulating a frequency with which a second sensor generates one or more measurements of a second physiological parameter over an interval of time corresponding to the variation, so as to increase insight into the second physiological parameter as the individual experiences the change in health while conserving power when the individual is not experiencing variations in the first physiological parameter.

15. The non-transitory medium of claim 14, wherein the operations further comprise:

generating a report that specifies a relationship, if any, that exists between the first and second physiological parameters, as determined based on an analysis of the one or more measurements corresponding to the interval of time.

16. The non-transitory medium of claim 15, wherein the report is accessible to a person other than the individual.

17. The non-transitory medium of claim 14, wherein the variation is identified by:

applying, to the measurements, an algorithm that identifies at least one measurement that matches a pattern in accordance with a pattern-defining parameter; and characterizing the at least one measurement as being indicative of the variation.

18. The non-transitory medium of claim 14, wherein the variation is identified by:

applying, to the measurements, patterns that correspond to different types of physiological events; and characterizing the variation as representative of a given type of physiological event by identifying a matching one of the patterns.

19. The non-transitory medium of claim 14, wherein the operations further comprise:

modulating a frequency with which the first sensor generates one or more measurements for the first physiological parameter over the interval of time corresponding to the variation, so as to also increase insight into the first physiological parameter as the individual experiences the change in health.

20. The non-transitory medium of claim 1, wherein said altering causes a resolution and/or a polling frequency of the sensor to be highest within the interval of time that includes, or is expected to include, the potential instance of the glycemic event.

* * * * *